United States Patent
Kobayashi et al.

(10) Patent No.: US 11,413,059 B2
(45) Date of Patent: Aug. 16, 2022

(54) ENERGY SURGICAL INSTRUMENT

(71) Applicant: OLYMPUS CORPORATION, Hachioji (JP)

(72) Inventors: Marina Kobayashi, Hachioji (JP); Yuji Hirai, Sagamihara (JP); Satomi Sakao, Hachioji (JP); Takeshi Onaga, Koshigaya (JP); Kazuhiro Morisaki, Yokohama (JP); Katsushi Ide, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 1017 days.

(21) Appl. No.: 15/998,418

(22) Filed: Aug. 15, 2018

(65) Prior Publication Data
US 2019/0021757 A1 Jan. 24, 2019

Related U.S. Application Data

(63) Continuation of application No. PCT/JP2016/054310, filed on Feb. 15, 2016.

(51) Int. Cl.
*A61B 18/14* (2006.01)
*A61B 17/32* (2006.01)
(Continued)

(52) U.S. Cl.
CPC .. *A61B 17/320092* (2013.01); *A61B 18/1445* (2013.01); *A61B 2017/00057* (2013.01);
(Continued)

(58) Field of Classification Search
CPC ...... A61B 2090/034; A61B 17/320092; A61B 2017/320082; A61B 2017/320095; A61B 18/1442–1447; A61B 2018/145–146
See application file for complete search history.

(56) References Cited

U.S. PATENT DOCUMENTS 6,569,178 B1 * 5/2003 Miyawaki ...... A61B 17/320092
606/169
2004/0243125 A1 12/2004 Dycus et al.
(Continued)

FOREIGN PATENT DOCUMENTS

JP 2005-512606 A 5/2005
JP 2005-349022 A 12/2005
(Continued)

OTHER PUBLICATIONS

Jun. 1, 2020 Office Action issued in Chinese Patent Application No. 201680081866.7.
(Continued)

*Primary Examiner* — Joanne M Hoffman
*Assistant Examiner* — Sean W Collins
(74) *Attorney, Agent, or Firm* — Oliff PLC

(57) ABSTRACT

An energy surgical instrument includes first and second grasping pieces for grasping a blood vessel. At least one of the grasping pieces is designed to apply treatment energy to a grasped blood vessel. The instrument also includes a processor designed to set a wall thickness of the blood vessel, and a grasping force adjuster designed to adjust a grasping force applied by the first and second grasping pieces. A first grasping force is applied when the wall thickness set by the processor is larger than a predetermined thickness, and a second grasping force, which is larger than the first grasping force, is applied when the wall thickness set by the processor is equal to or smaller than the predetermined thickness. A treatment method includes applying treatment energy to a blood vessel grasped by the first and second grasping pieces of the instrument to seal the blood vessel.

18 Claims, 10 Drawing Sheets

(51) Int. Cl.
A61B 17/00 (2006.01)
A61B 90/00 (2016.01)
A61B 18/00 (2006.01)

(52) U.S. Cl.
CPC ........ *A61B 2017/00398* (2013.01); *A61B 2017/00778* (2013.01); *A61B 2017/320082* (2017.08); *A61B 2017/320095* (2017.08); *A61B 2018/0063* (2013.01); *A61B 2018/00404* (2013.01); *A61B 2018/00589* (2013.01); *A61B 2018/00601* (2013.01); *A61B 2018/00607* (2013.01); *A61B 2018/00994* (2013.01); *A61B 2090/034* (2016.02); *A61B 2090/064* (2016.02); *A61B 2090/067* (2016.02)

(56) References Cited

U.S. PATENT DOCUMENTS

| | | |
|---|---|---|
| 2008/0039836 A1 | 2/2008 | Odom et al. |
| 2011/0118736 A1 | 5/2011 | Harper et al. |
| 2012/0116394 A1* | 5/2012 | Timm .................. A61B 90/40 606/45 |
| 2014/0074122 A1* | 3/2014 | Whelan ............... A61B 17/122 606/139 |

FOREIGN PATENT DOCUMENTS

| | | |
|---|---|---|
| JP | 2008-036441 A | 2/2008 |
| JP | 2011-104376 A | 6/2011 |

OTHER PUBLICATIONS

May 17, 2016 International Search Report issued in Patent Application No. PCT/JP2016/054310.

\* cited by examiner

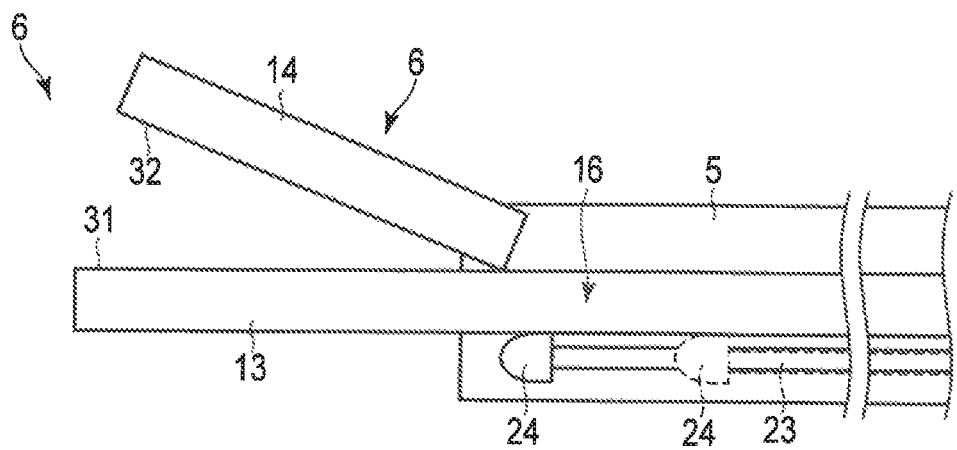
F I G. 5
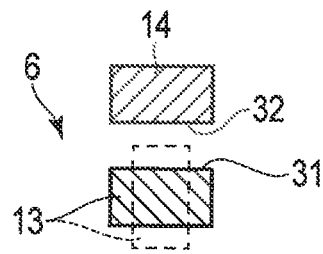
F I G. 6
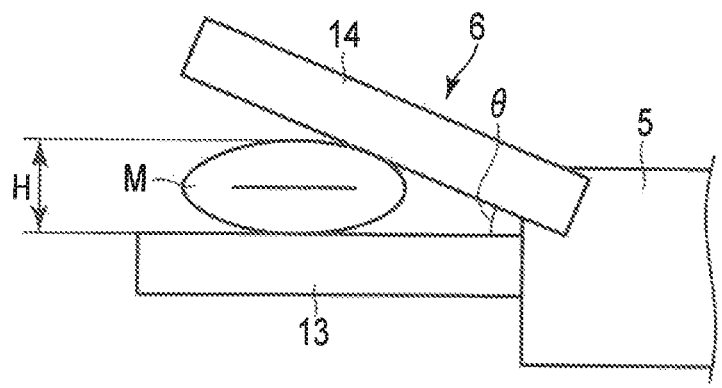
F I G. 7

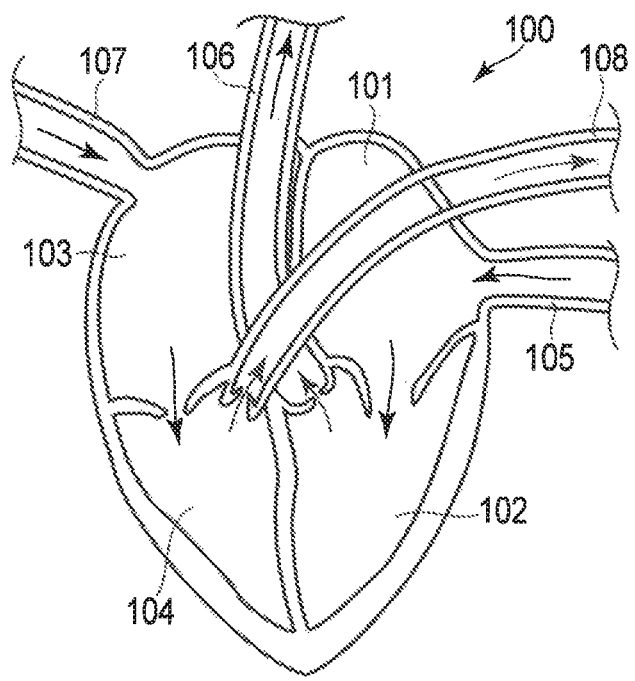
F I G. 17
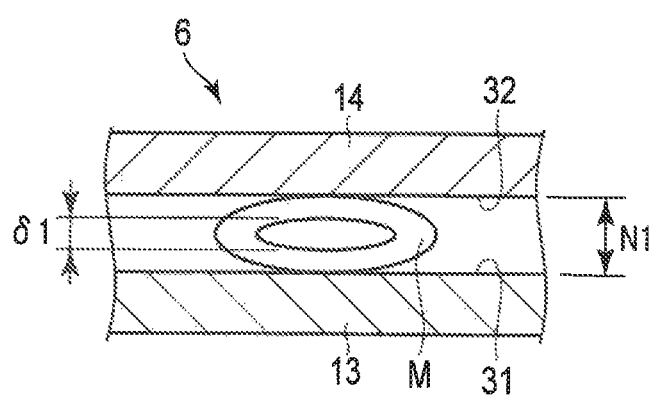
F I G. 18

ENERGY SURGICAL INSTRUMENT

This is a Continuation Application of PCT Application No. PCT/JP2016/054310, filed Feb. 15, 2016, the entire contents of which are incorporated herein by reference.

BACKGROUND

Exemplary embodiments relate to an energy surgical instrument which grasps a treatment target such as living tissue between a pair of grasping pieces to conduct treatment using treatment energy such as an ultrasonic vibration and a high-frequency current.

For example, US 2011/0118736 discloses an energy surgical instrument which grasps a treatment target such as living tissue between a pair of grasping pieces and applies treatment energy to the grasped treatment target to allow the treatment target to be sealed.

SUMMARY

According to an exemplary embodiment, an energy surgical instrument includes a first grasping piece, a second grasping piece which is allowed to open and close relative to the first grasping piece and which is allowed to grasp a blood vessel between the first grasping piece and the second grasping piece, an energy application unit provided in at least one of the first grasping piece and the second grasping piece, which applies treatment energy to the blood vessel grasped between the first grasping piece and the second grasping piece to treat the blood vessel, a setting unit which sets information regarding a wall thickness of the blood vessel, and a grasping force adjustment unit which adjusts a grasping force to grasp the blood vessel between the first grasping piece and the second grasping piece to a first grasping force when the wall thickness set by the setting unit is larger than a predetermined thickness and adjusting the grasping force to a second grasping force, which is larger than the first grasping force, when the wall thickness set by the setting unit is equal to or smaller than the predetermined thickness.

Advantages will be set forth in the description which follows, and in part will be apparent from the description, or may be learned by practice of exemplary embodiments. The advantages may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate exemplary embodiments.

FIG. 5 is a schematic view showing the interior of a sheath and a configuration of an end effector according to an exemplary embodiment.

FIG. 6 is a schematic cross-sectional view showing an end effector according to an exemplary embodiment, which is substantially perpendicular to a longitudinal axis thereof.

FIG. 7 is a schematic view showing an end effector according to an exemplary embodiment, by which a blood vessel is grasped.

FIG. 17 is a schematic view showing a structure of a heart and its neighborhood.

FIG. 18 is a schematic view showing the end effector according to an exemplary embodiment, by which a blood vessel is grasped with a first grasping force.

DETAILED DESCRIPTION

Figure 1:
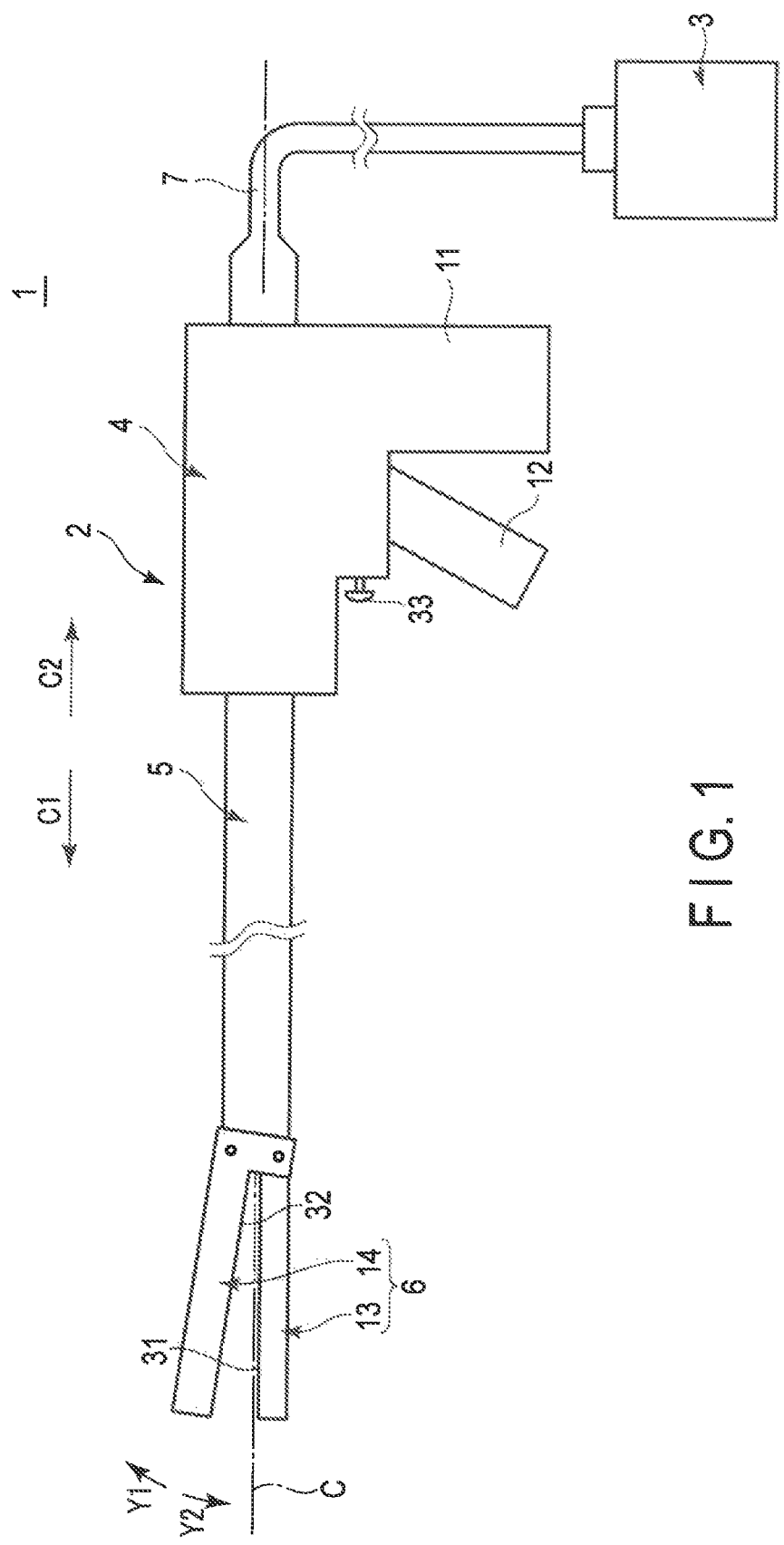
FIG. 1 is a schematic view showing an outward appearance of an energy surgical instrument according to an exemplary embodiment.

Embodiments and the like of the energy surgical instrument will be described below with reference to FIGS. 1-19. FIG. 1 is a view showing an outward appearance of an energy surgical instrument (treatment system) 1 according to an exemplary embodiment. As shown in FIG. 1, the energy surgical instrument 1 includes an energy treatment instrument 2 and an energy controller 3. The energy treatment instrument 2 has a longitudinal axis C. Here, one side of the direction along the longitudinal axis C is defined as a distal side (arrow C1 side) and the side opposite to the distal side is defined as a proximal side (arrow C2 side). The direction that is parallel to the longitudinal axis C is defined as a longitudinal direction.

The energy treatment instrument 2 includes a holdable housing 4. A sheath 5 extends along the longitudinal axis C and is inserted into the housing 4 from the distal side. The central axis of the sheath 5 is substantially aligned with the longitudinal axis C. An end effector 6 is provided at a distal portion of the sheath 5. One end of a cable 7 is connected to the housing 4. The other end of the cable 7 is separably connected to the energy controller 3.

The housing 4 includes a grip 11. A handle 12 is revolvably attached to the housing 4. The handle 12 revolves relative to the housing 4 and thus opens or closes relative to the grip 11. In the present embodiment, the handle 12 is located on the distal side of the grip 11, which is, however, not restrictive. In another embodiment, for example, the handle 12 may be located on the proximal side of the grip 11. Furthermore, in the present embodiment, the handle 12 can open and close in a direction substantially parallel to the longitudinal axis C relative to the grip 11, which is, however, not restrictive. In another certain example, the handle 12 may open and close in a direction substantially perpendicularly to the longitudinal axis C relative to the grip 11.

The end effector 6 includes a first grasping piece 13 and a second grasping piece 14 which can open and close relative to the first grasping piece 13. The first grasping piece 13 has a first opposing surface 31 opposed to the second grasping piece 14. The second grasping piece 14 has a second opposing surface 32 opposed to the first grasping piece 13 (first opposing surface 31). The handle 12 opens or closes relative to the grip 11 and accordingly the paired grasping pieces 13 and 14 open or close relative to each other. If the paired grasping pieces 13 and 14 close relative to each other, a blood vessel can be grasped between the first grasping piece 13 (first opposing surface 31) and the second grasping piece 14 (second opposing surface 32) as a treatment target. Here, an area between the first and second grasping pieces 13 and 14, which are closed relative to each other, is defined as a grasping area. The direction which is substantially perpendicular to (crosses) the longitudinal axis C and substantially perpendicular to (crosses) the open and close directions (directions of arrows Y1 and Y2) of each of the grasping pieces 13 and 14 in the end effector 6 is defined as a width direction of the end effector 6 (first and second grasping pieces 13 and 14).

The end effector 6 has only to be so configured that a treatment target can be grasped between the grasping pieces 13 and 14. In a certain example, one of the first and second grasping pieces 13 and 14 is provided as a distal portion of a rod member (not shown) inserted through the sheath 5 along the longitudinal axis C and a protruding portion that protrudes toward the distal side from the distal end of the sheath 5. The other of the first and second grasping pieces 13 and 14 is revolvably attached to the distal portion of the sheath 5. In another certain example, one of the first and second grasping pieces 13 and 14 is provided integrally with the sheath 5. The other of the first and second grasping pieces 13 and 14 is revolvably attached to the distal portion of the sheath 5. In still another certain example, both of the first and second grasping pieces 13 and 14 are revolvably attached to the distal portion of the sheath 5.

Figure 2:
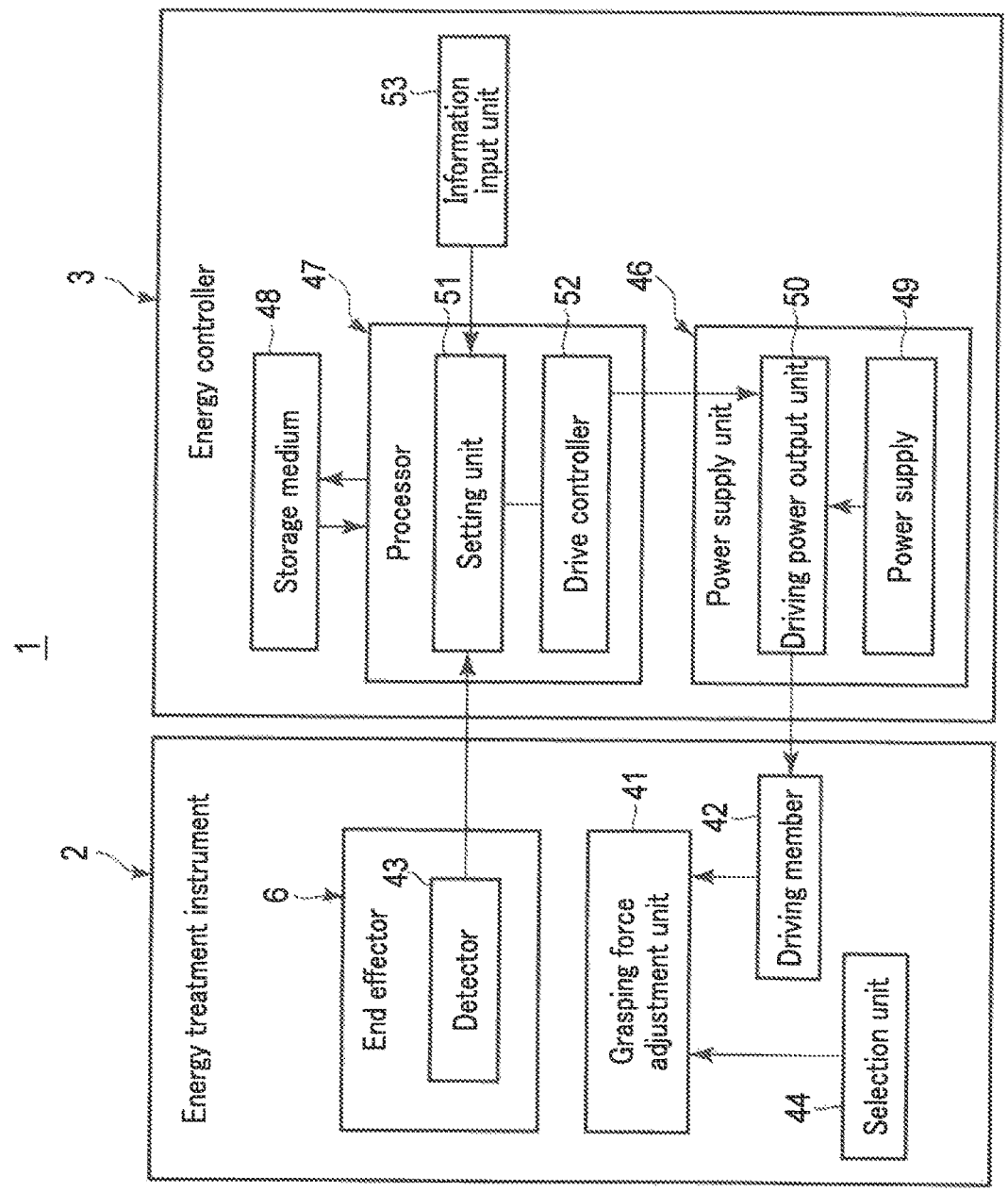
FIG. 2 is a block diagram schematically showing an actuation configuration and a control configuration of the energy surgical instrument according to an exemplary embodiment.

FIG. 2 is a block diagram schematically showing an actuation configuration and a control configuration of the energy surgical instrument 1. As shown in FIG. 2, the energy treatment instrument 2 includes a grasping force adjustment unit 41 that adjusts grasping force to be applied to a treatment target grasped between the grasping pieces 13 and 14 and a driving member 42 such as an electric motor. The actuation state of the grasping force adjustment unit 41 varies with the driving state of the driving member 42. The end effector 6 also includes a detector 43 that detects information about a blood vessel grasped between the grasping pieces 13 and 14. The grasping force adjustment unit 41 and the detector 43 will be described in detail later.

The energy controller 3 includes a power supply unit 46, a processor (or an integrated circuit, etc.) 47 with a central processing unit (CPU), an application specific integrated circuit (ASIC) or the like and a storage medium 48 such as a memory. The power supply unit 46 includes a power supply 49 such as a battery and an outlet and a driving power output unit 50 that outputs driving power of the driving member 42. The driving power output unit 50 includes, e.g. a conversion circuit that converts power from the power supply 49 into driving power and supplies the driving power to the driving member 42.

The processor 47 includes a setting unit 51 and a drive controller 52. The setting unit 51 and drive controller 52 perform part of the process to be performed by the processor 47. The setting unit 51 sets information about wall thickness T of a blood vessel to be grasped, based upon information (parameter) about a blood vessel detected by the detector 43. In this instance, the setting unit 51 may set wall thickness T of the blood vessel itself and set whether the wall thickness T of the blood vessel is greater than a predetermined thickness Tth. The setting unit 51 may also set a type of the blood vessel (a systemic circulatory system or a pulmonary circulatory system). Note that the predetermined thickness Tth is stored in the storage medium 48, etc. In a certain example, furthermore, the energy controller 3 is provided with a notification unit (not shown) such as a display and a buzzer, and the notification unit may notify the information about the wall thickness T of the blood vessel set by the setting unit 51.

In accordance with the information about the wall thickness T set by the setting unit 51, the drive controller 52 determines a parameter regarding the grasping force applied to a treatment target grasped between the grasping pieces 13 and 14. Then, based upon the determined parameter regarding the grasping force, the drive controller 52 controls the supply of driving power to the driving member 42 from the driving power output unit 50. Accordingly, the driving of the driving member 42 is controlled, as is the actuation of the grasping force adjustment unit 41. When the actuation of the grasping force adjustment unit 41 is controlled, the grasping force applied to the treatment target between the grasping pieces 13 and 14 is adjusted.

In the present embodiment, the detector 43 detects information about a blood vessel to be grasped between the grasping pieces 13 and 14, which is, however, not restrictive. In a certain example, for example, the energy controller 3 can be provided with an information input unit 53 such as an operating panel to input information about a blood vessel manually. In this case, a surgeon operates the information input unit 53 to input information about a blood vessel. Thus, the setting unit 51 sets information about wall thickness T of a blood vessel to be grasped, based upon an input result of the information input unit 53 (information about a blood vessel input to the information input unit 53).

In the present embodiment, in accordance with the information about wall thickness T set by the setting unit 51, the processor 47 controls the actuation of the grasping force adjustment unit 41 to adjust the grasping force applied to the blood vessel between the grasping pieces 13 and 14, which is, however, not restrictive. In a certain example, for example, the housing 4 of the energy treatment instrument 2 can be provided with a selection unit 44 such as a lever to select an actuation state of the grasping force adjustment unit 41 manually. In this case, in accordance with the information about wall thickness T of a blood vessel set by the setting unit 51, the surgeon operates the selection unit 44 to adjust the actuation state of the grasping force adjustment unit 41. Accordingly, the grasping force to be applied to the blood vessel between the grasping pieces 13 and 14 is adjusted.

Furthermore, when a treatment target is grasped between the first and second grasping pieces 13 and 14, the first and second opposing surfaces 31 and 32 are brought into contact with the treatment target. Then, at least one of the first and second opposing surfaces 31 and 32 applies treatment energy to the treatment target grasped between the first and second grasping pieces 13 and 14 to seal (coagulate) the treatment target. In other words, at least one of the first and second grasping pieces 13 and 14 is provided with an energy application section (31; 32; 31, 32) which applies treatment energy to the grasped treatment target.

An operational button 33 is attached to the housing 4 as an energy operation input section. The power supply unit 46 of the energy controller 3 is provided with an energy output unit (not shown) which outputs electrical energy other than the driving power to the energy treatment instrument 2. The energy output unit includes, e.g. a conversion circuit that converts power from the power supply 49 into electrical energy and supplies the electrical energy to the energy treatment instrument 2. Upon detecting operation input of the operation button 33, the processor 47 causes the power supply unit 46 to output the foregoing electrical energy to the energy treatment instrument 2.

Note that the energy operation input section to perform an operation of outputting electrical energy from the energy controller 3 is not limited to the operation button 33. In a certain example, in place of the operation button 33 or in addition to the operation button 33, for example, a foot switch separate from the energy treatment instrument 2 can be provided as the energy operation input section. In the present embodiment, furthermore, the electrical energy output from the energy output unit of the power supply unit 46 can be directly applied to a blood vessel to be grasped as treatment energy, and the foregoing electrical energy can be converted into treatment energy such as an ultrasonic vibration and the treatment energy can be applied to a treatment target.

In a certain example, an ultrasonic vibration is applied to a treatment target as treatment energy. In this instance, an ultrasonic transducer (not shown) is provided in the interior of the housing 4 and a rod member (not shown) is inserted through the sheath 5 as a vibration transmission member. In the interior of the housing 4, the rod member is connected to the distal side of the ultrasonic transducer and accordingly, the first grasping piece 13 is formed by a portion of the rod member protruding from the sheath 5 toward the distal side. In this example, when the electrical energy (AC power) output from the power supply unit 46 of the energy controller 3 is supplied to the ultrasonic transducer, the ultrasonic transducer generates an ultrasonic vibration. The generated ultrasonic vibration is transmitted from the proximal side to the distal side of the rod member (vibration transmission member) to vibrate the rod member including the first grasping piece 13. When the rod member is vibrated with the treatment target grasped between the first and second grasping pieces 13 and 14, the ultrasonic vibration is applied to the treatment target as treatment energy through the first opposing surface (energy application section) 31 of the first grasping piece 13. In this instance, the vibration causes frictional heat between the treatment target to be grasped and the first grasping piece 13, and the treatment target is cut open and sealed (coagulated) simultaneously.

In another certain example, a high-frequency current is supplied to a treatment target as treatment energy. In this case, the first and second grasping pieces 13 and 14 are provided with their respective electrodes, and electrical energy (high-frequency power) are applied to these electrodes from the power supply unit 46 of the energy controller 3. When the electrical energy is applied to the electrodes with the treatment target grasped between the first and second grasping pieces 13 and 14, a high-frequency current flows through the treatment target between the electrodes. In other words, a high-frequency current is supplied as treatment energy to a treatment target to be grasped, through the first and second opposing surfaces 31 and 32 of the first and second grasping pieces 13 and 14, which are energy application sections. When a high-frequency current flows through the treatment target, heat is generated from the treatment target and the treatment target is coagulated by the generated heat. In this example, at least one of the first and second opposing surfaces 31 and 32 is provided with a contact section that is made of an electrically insulating material. Thus, the electrodes are prevented from being in contact with each other, and a short circuit is prevented from occurring in an electrical path of the high-frequency current flowing through the treatment target.

In a certain example, the first and second grasping pieces 13 and 14 can be provided with, for example, a cutter (not shown) that is movable along the longitudinal axis C, in addition to the foregoing electrodes. In this case, when the cutter is moved, a treatment target to be grasped is cut open and simultaneously a high-frequency current is caused to flow through the treatment target as described above to seal (bond) the treatment target.

In another certain example, at least one of the first and second grasping pieces 13 and 14 is provided with a heating element (not shown). In the present example, when electrical energy (DC power or AC power) is supplied to the heating element from the power supply unit 46 of the energy controller 3, the heating element generates heat. When the heating element generates heat with a treatment target grasped between the first and second grasping pieces 13 and 14, the generated heat is supplied to the treatment target through at least one of the first opposing surface (energy application section) 31 and the second opposing surface (energy application section) 32. When the heat generated from the heating element is supplied to the treatment target as treatment energy, the treatment target is cut open and coagulated simultaneously.

Some of the treatment energies such as the ultrasonic vibration, high-frequency current and heat generated from the heating element can be applied simultaneously to a treatment target to be grasped. In a certain example, the ultrasonic vibration and high-frequency current are applied as treatment energy to a treatment target simultaneously. In this case, when electrical energy is supplied to the foregoing ultrasonic transducer from the power supply unit 46 of the energy controller 3, an ultrasonic vibration is generated and simultaneously electrical energy is supplied to the electrodes of the first and second grasping pieces 13 and 14 from the power supply unit 46 of the energy controller 3. In another certain example, the high-frequency current as treatment energy and heat generated from the heating element as treatment energy are supplied to a treatment target simultaneously. In this case, when electrical energy is supplied to the foregoing heating element from the power supply unit 46 of the energy controller 3, heat is generated and simultaneously electrical energy is supplied to the electrodes of the first and second grasping pieces 13 and 14 from the power supply unit 46 of the energy controller 3.

Figure 3:
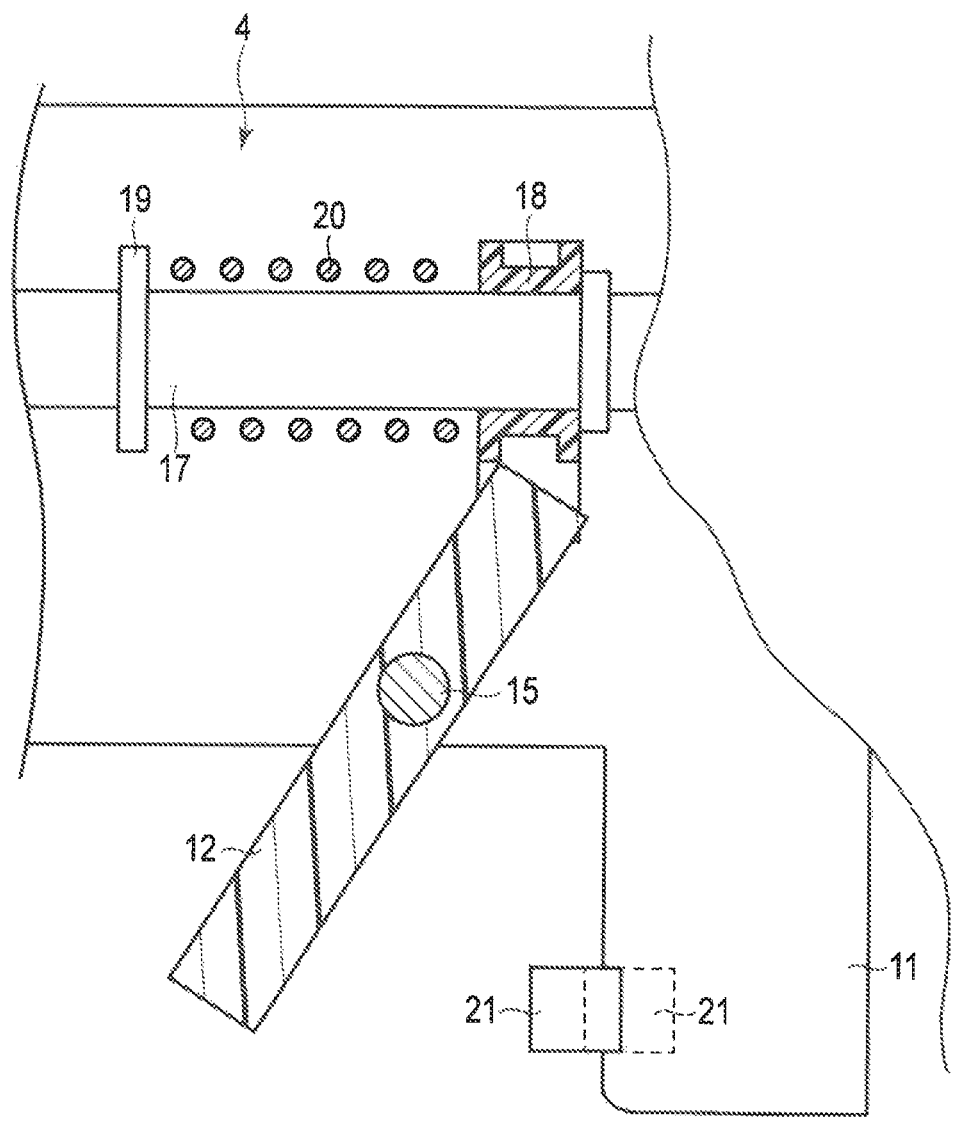
FIG. 3 is a schematic view showing an internal configuration of a housing according to an exemplary embodiment.

Next, the grasping force adjustment unit 41 will be described. FIG. 3 is a view showing an internal configuration of the housing 4. As shown in FIG. 3, a movable member 17 extends along the longitudinal axis C in the interior of the housing 4. The movable member 17 is movable along the longitudinal axis C relative to the housing 4. The movable member 17 is coupled to at least one of the first and second grasping pieces 13 and 14 via a movable pipe (not shown) extending along the longitudinal axis C in the interior of the sheath 5. For example, in a certain example, when the movable member 17 moves to the distal side relative to the housing 4, at least one of the first and second grasping pieces 13 and 14 operates to close relative to the other. When the movable member 17 moves the proximal side relative to the housing 4, at least one of the first and second grasping pieces 13 and 14 operates to open relative to the other. In other words, when the movable member 17 moves along the longitudinal axis C relative to the housing 4 and the sheath 5, the paired grasping pieces 13 and 14 open or close relative to each other.

The movable member 17 is provided with a protruding section 19 that protrudes toward the outer side thereof. On the outer side of the movable member 17, a slide member 18 is disposed away from the protruding section 19 toward the proximal side. Between the protruding section 19 and the slide member 18, a coil spring 20 of an elastic member is provided. The proximal end of the coil spring 20 is connected to the slide member 18 and the distal end thereof is connected to the protruding section 19. The length of the coil spring 20 is L0 in its natural state. When no treatment target is placed between the grasping pieces 13 and 14, the coil spring 20 is attached in a reference state where it is contracted by displacement amount x0 from the natural state. In this instance, if the elastic coefficient of the coil spring 20 is k0, elastic force k0x0 is exerted on the movable member 17 from the coil spring 20.

The handle 12 is coupled to the slide member 18. The handle 12 is also coupled to the housing 4 via a fulcrum pin 15. The handle 12 revolves on the fulcrum pin 15 relative to the housing 4 and opens or closes relative to the grip 11. The grip 11 is provided with an abutting member 21. When the handle 12 closes relative to the grip 11, the handle 12 abuts on the abutting member 21.

To grasp a treatment target between the grasping pieces 13 and 14, a surgeon holds the grip 11 and presses the handle 12 toward the grip 11. Then, the surgeon operates to close the handle 12 relative to the grip 11 until the handle 12 abuts on the abutting member 21 of the grip 11. Accordingly, the handle 12 revolves on the fulcrum pin 15 and simultaneously the slide member 18, movable member 17 and movable pipe (not shown) move integrally to the distal side along the longitudinal direction. Thus, at least one of the grasping pieces 13 and 14 operates to close relative to the other. In other words, the end effector 6 operates to close. Until a treatment target to be grasped is contracted to some extent in the open and close direction of the end effector 6, the coil spring 20 is not contracted from a reference state, and the elastic force that is exerted on the movable member 17 from the coil spring 20 does not vary from k0x0.

When the treatment target to be grasped is contracted to some extent in the open and close direction of the end effector 6, the end effector 6 stops operating to close. The movable pipe and the movable member 17 thus stop moving to the distal side. If the handle 12 is operated to close relative to the grip 11 until the handle 12 abuts on the abutting member 21 of the grip 11 from this state, the slide member 18 moves to the distal side relative to the movable member 17. When the slide member 18 moves to the distal side relative to the movable member 17, the coil spring 20 is contracted further from the reference state. If the displacement amount (contraction amount) of the coil spring 20 from the reference state is x, the elastic force that is exerted on the movable member 17 from the coil spring 20 when the coil spring 20 is contracted further from the reference state is $k0(x0+x)$, which is larger than the elastic force $k0x0$ in the reference state. When the elastic force $k0(x0+x)$ that is larger than the elastic force $k0x0$ in the reference state is exerted on the movable member 17 from the coil spring 20, the grasping force applied to the treatment target to be grasped between the first and second grasping pieces 13 and 14 increases in comparison with the case where the coil spring 20 is in the reference state. In other words, the grasping force applied to the treatment target to be grasped between the paired grasping pieces 13 and 14 is determined in accordance with the displacement amount (contraction amount) x by which the coil spring 20 is contracted.

The grasping force adjustment unit 41 adjusts the grasping force applied to the treatment target to be grasped between the grasping pieces 13 and 14. In a certain example, the foregoing abutting member 21 provided at the grip 11 corresponds to the grasping force adjustment unit 41. The driving member 42 (see FIG. 2) provided in the interior of the housing 4 is driven to move the abutting member 21 in the longitudinal direction relative to the grip 11. As the driving member 42, for example, an electric motor is used. In another example, the selection unit 44 (see FIG. 2) such as a lever can be attached to the housing 4 and operated manually to move the abutting member 21 in the longitudinal direction relative to the grip 11.

When the abutting member 21 moves in the longitudinal direction relative to the grip 11 and thus the handle 12 operates to close relative to the grip 11, the movement amount (stroke) by which the handle 12 moves until the handle 12 abuts on the abutting member 21 varies. Accordingly, the movement amount by which the slide member 18 coupled to the handle 12 moves in the longitudinal direction relative to the movable member 17 varies. As the movement amount by which the slide member 18 moves relative to the movable member 17 varies, the displacement amount (contraction amount) of the coil spring 20 varies. As describe above, the grasping force applied to the treatment target is determined by the displacement amount of the coil spring 20. The grasping force applied to the treatment target can thus be varied by varying the position of the abutting member 21. For example, when the abutting member 21 is located in a first position (indicated by the solid line in FIG. 3), the coil spring 20 is contracted by displacement amount x1 from the reference state with the handle 12 abutting on the abutting member 21. Thus, the elastic force $k0(x0+x1)$ is exerted on the movable member 17 from the coil spring 20, and the grasping force to grasp a blood vessel between the grasping pieces 13 and 14 is a first grasping force. When the abutting member 21 is located in a second position (indicated by the broken line in FIG. 3) which is closer to the proximal side than the first position, the coil spring 20 is contracted by displacement amount x2 that is larger than the amount x1 from the reference state with the handle 12 abutting on the abutting member 21. Thus, the elastic force $k0(x0+x2)$, which is larger than the elastic force $k0(x0+x1)$, is exerted on the movable member 17 from the coil spring 20, and the grasping force to grasp a blood vessel between the grasping pieces 13 and 14 is a second grasping force that is larger than the first grasping force. As described above, in the present example, the driving member 42 or the selection unit 44 varies the position of the abutting member 21 that is the grasping force adjustment unit 41 to vary the grasping force to be applied to the treatment target.

Figure 4:
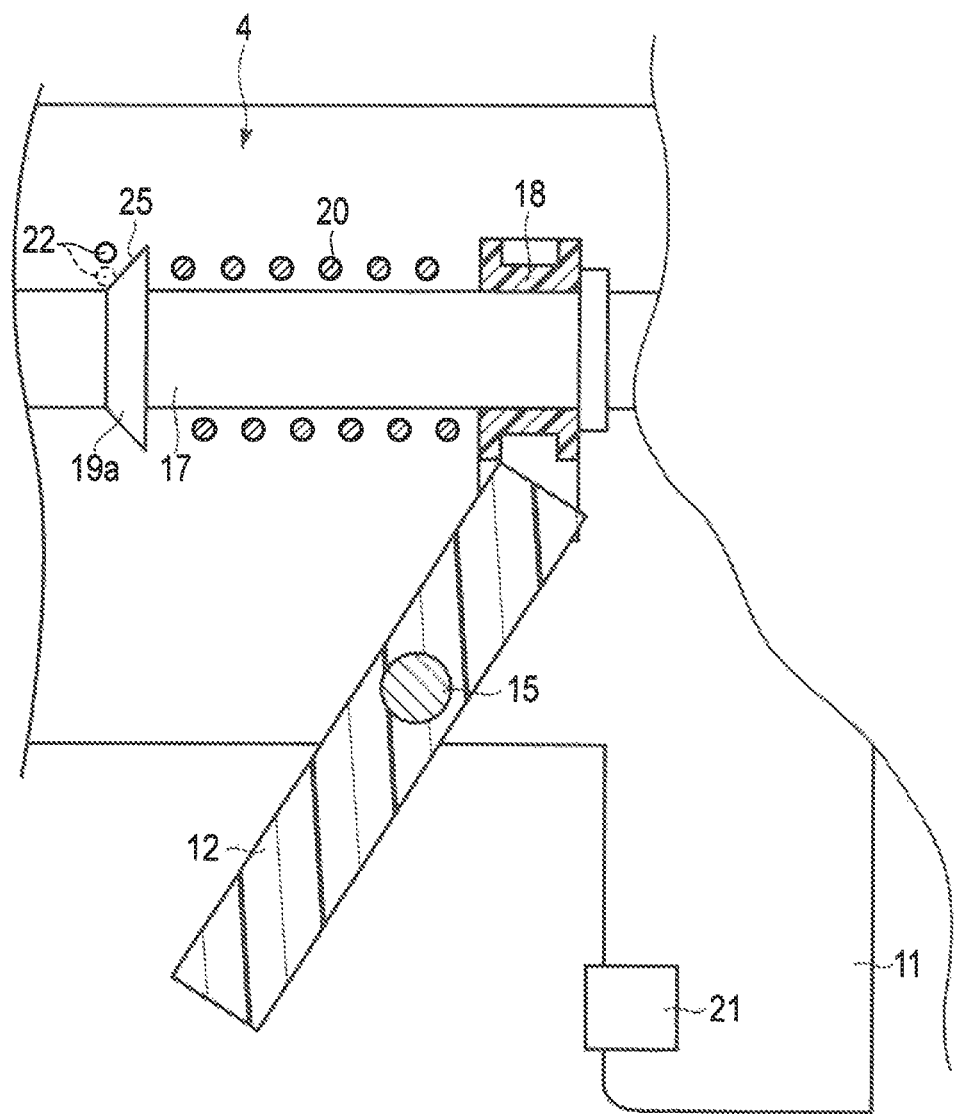
FIG. 4 is a schematic view showing an internal configuration of a housing according to an exemplary embodiment.

In another exemplary embodiment, a rod-like member 22 can be provided as the grasping force adjustment unit 41 as shown in FIG. 4. FIG. 4 is a view showing an internal configuration of the housing 4 according to the present embodiment. As shown in FIG. 4, in place of the protruding section 19, a ring-like member 19a is provided on the outer side of the movable member 17 along the circumferential direction of the movable member 17 (axial rotation direction). One end (distal end) of the coil spring 20 is connected to the ring-like member 19a. The ring-like member 19a has an inclined surface 25 that inclines toward the inner side in the distal side direction. The rod-like member 22 abuts on the ring-like member 19a from its distal side. In a certain example, the driving member 42 (see FIG. 2) is provided in the interior of the housing 4, and the rod-like member 22 is moved in the radial direction of the ring-like member 19a by driving the driving member 42. The rod-like member 22 abuts on the inclined surface 25 to regulate the movement of the ring-like member 19a to the distal side. As the driving member 42, for example, an electric motor is used. In another certain example, the selection unit 44 (see FIG. 2) such as a lever can be attached to the housing 4 and operated manually to move the rod-like member 22 in the radial direction of the ring-like member 19a.

In the coil spring 20 of the present embodiment, the displacement amount (contraction amount) x0 from the natural state varies in a state where no treatment target is interposed between the grasping pieces 13 and 14 (namely, a reference state), in accordance with the position of the rod-like member 22 in its radial direction. For example, when the rod-like member 22 is located in a first position (indicated by the solid line in FIG. 4) of the ring-like member 19a, the coil spring 20 is contracted by the displacement amount xa0 from the natural state in the reference state. Accordingly, in the reference state, the elastic force k0xa0 is exerted on the movable member 17 from the coil spring 20. When the coil spring 20 is contracted further from the reference state, the elastic force k0(xa0+x) is exerted on the movable member 17 from the coil spring 20. When the rod-like member 22 is located in a second position (indicated by the broken line in FIG. 4) which is inside the first position in the radial direction of the ring-like member 19a, pressure force exerted on the ring-like member 19a from the rod-like member 22 becomes larger than that in the case where the rod-like member 22 is located in the first position. Therefore, when the rod-like member 22 is located in the second position, the ring-like member 19a is located on the proximal side as compared with the case where the rod-like member 22 is located in the first position. When the rod-like member 22 is located in the second position, the coil spring 20 is contracted by the displacement amount xb0, which is larger than the displacement amount xa0, from the natural state in the reference state. Thus, the elastic force k0xb0 that is larger than the elastic force k0xa0 is exerted on the movable member 17 from the coil spring 20 in the reference state. When the coil spring 20 is contracted further from the reference state, the elastic force k0(xb0+x), which is larger than the elastic force k0(xa0+x), is exerted on the movable member 17 from the coil spring 20.

Therefore, when the rod-like member 22 is located in the second position, the grasping force to be applied to the treatment target becomes larger than that in the case where the rod-like member 22 is located in the first position. For example, the grasping force to grasp a blood vessel between the grasping pieces 13 and 14 is a first grasping force when the rod-like member 22 is located in the first position, and the grasping force to grasp a blood vessel between the grasping pieces 13 and 14 is a second grasping force that is larger than the first grasping force when the rod-like member 22 is located in the second position. As described above, in the present embodiment, the rod-like member 22 corresponds to the grasping force adjustment unit 41, and the driving member 42 or the selection unit 44 move the rod-like member 22 in the radial direction of the ring-like member 19a to allow the grasping force applied to the treatment target to vary.

According to another exemplary embodiment shown in FIG. 5, a bar member 23 and a stopper 24 can be provided as the grasping force adjustment unit 41. FIG. 5 is a view showing the interior of the sheath 5 and a configuration of the end effector 6 according to the present embodiment. As shown in FIG. 5, the end effector 6 includes a first grasping piece 13 provided at a distal portion of the rod member 16 inserted through the sheath 5 and a second grasping piece 14 revolvably coupled to a distal portion of the sheath 5. In other words, one of the paired grasping pieces 13 and 14 revolves relative to the other. The bar member 23 extends along the longitudinal direction in the interior of the sheath 5. The bar member 23 is provided on the side opposite to the first opposing surface 31 with respect to the longitudinal axis C. In a certain example, the driving member 42 (see FIG. 2) is provided in the interior of the housing 4 and driven to move the bar member 23 in the longitudinal direction relative to the rod member 16. As the driving member 42, for example, an electric motor is used. In another certain example, the selection unit 44 (see FIG. 2) such as a lever can be attached to the housing 4 and operated manually to move the bar member 23 in the longitudinal direction relative to the rod member 16. The stopper 24, which abuts on the outer surface of the rod member 16, is provided at a distal portion of the bar member 23. The stopper 24 is formed of, e.g. polytetrafluoroethylene (PTFE) that is excellent in abrasion resistance. The stopper 24 is disposed between the rod member 16 and the sheath 5. In a position where the stopper 24 abuts on the rod member 16, the rod member 16 is supported in the open direction of the second grasping piece 14. In the position where the stopper 24 abuts on the rod member 16, the rod member 16 is prevented from bending in the close direction of the second grasping piece 14.

When the second grasping piece 14 is closed relative to the first grasping piece 13, the first grasping piece 13 and the rod member 16 receive pressure force from the second grasping piece 14 in the close direction of the second grasping piece 14. Then, the rod member 16 is bent (curved) toward the close direction of the second grasping piece 14 from a position in which the rod member 16 is supported by the stopper 24 to the distal end of the rod member 16. In other words, a portion from a position in which the rod member 16 is supported by the stopper 24 to the distal end of the rod member 16 is bent by the pressure force in the close direction of the second grasping piece 14. The grasping force applied to the treatment target to be grasped between the first and second grasping pieces 13 and 14 varies with the amount of bent of the first grasping piece 13 in the close direction of the second grasping piece 14.

In the present embodiment, the bar member 23 and the stopper 24 correspond to the grasping force adjustment unit 41. The bar member 23 and the stopper 24 move integrally in the longitudinal direction relative to the rod member 16 to vary a position in which the rod member 16 is supported by the stopper 24. When a position in which the rod member 16 is supported by the stopper 24 varies, the length from the position in which the rod member 16 is supported by the stopper 24 to the distal end of the rod member 16 varies, as does the amount of bent of the first grasping piece 13 in the close direction of the second grasping piece 14. For example, when the stopper 24 is located in a first position (indicated by the broken line in FIG. 5), the rod member 16 has a first length from the position in which the rod member 16 is supported by the stopper 24 to the distal end of the rod member 16, and the amount of bent of the first grasping piece 13 in the close direction of the second grasping piece 14 is a first amount of bent. When the stopper 24 is located in a second position (indicated by the solid line in FIG. 5) which is closer to the distal side than the first position, the length from the position in which the rod member 16 is supported by the stopper 24 to the distal end of the rod member 16 is a second length that is smaller than the first length. The amount of bent of the first grasping piece 13 in the close direction of the second grasping piece 14 is a second amount of bent which is smaller than the first amount of bent.

For this reason, when the stopper 24 is located in the second position, the grasping force applied to the treatment target to be grasped between the first and second grasping pieces 13 and 14 becomes larger than that in the case where the stopper 24 is located in the first position. For example, the grasping force to grasp a blood vessel between the first and second grasping pieces 13 and 14 corresponds to a first grasping force when the stopper 24 is located in the first position, and the grasping force to grasp a blood vessel between the first and second grasping pieces 13 and 14 corresponds to a second grasping force that is larger than the first grasping force when the stopper 24 is located in the second position. As described above, in the present example, the bar member 23 and the stopper 24 correspond to the grasping force adjustment unit 41, and the driving member 42 or the selection unit 44 move the bar member 23 and the stopper 24 in the longitudinal direction relative to the rod member 16 to allow the grasping force applied to the treatment target to vary.

Furthermore, according to another exemplary embodiment shown in FIG. 6, a first grasping piece 13, which can be rotated in the axial rotation direction of the longitudinal axis C relative to the grasping piece 14, can be provided as the grasping force adjustment unit 41 (see FIG. 2). FIG. 6 is a cross-sectional view showing an end effector 6 according to the present embodiment, which is substantially parallel to the longitudinal axis C. In the present embodiment, a proximal end portion of the first grasping piece 13 is coupled to the driving member 42 (see FIG. 2), and the driving member 42 is driven to rotate the first grasping piece 13 in the axial rotation direction of the longitudinal axis C relative to the second grasping piece 14. When the first grasping piece rotates in the axial rotation direction of the longitudinal axis C relative to the second grasping piece 14, a surface that is to be the first opposing surface 31 opposed to the second opposing surface 32 is selected, and the first grasping piece 13 varies in its thickness in the open and close direction of the first grasping piece 13. As the driving member 42, for example, an electric motor is used. In another certain example, the selection unit 44 such as a lever can be attached to the housing 4 and operated manually to rotate the first grasping piece 13 in the axial rotation direction of the longitudinal axis C relative to the second grasping piece 14.

When the second grasping piece 14 is closed relative to the first grasping piece 13, the first grasping piece 13 receives pressure force from the second grasping piece 14 in the close direction of the second grasping piece 14. Then, the first grasping piece 13 is bent (curved) toward the close direction of the second grasping piece 14. The amount of bent of the first grasping piece 13 toward the close direction of the second grasping piece 14 varies with the thickness of the first grasping piece 13 in the open and close direction of the second grasping piece 14. The grasping force applied to the treatment target to be grasped between the first and second grasping pieces 13 and 14 varies with the amount of bent of the first grasping piece 13 in the close direction of the second grasping piece 14.

In the present embodiment, the first grasping piece 13 corresponds to the grasping force adjustment unit 41. When the first grasping piece 13 rotates in the axial rotation direction of the longitudinal axis C relative to the second grasping piece 14, a surface that is opposed to the second opposing surface 32 as the first opposing surface 31 is selected. When a surface that is opposed to the second opposing surface 32 as the first opposing surface 31 is selected, the first grasping piece 13 varies in its thickness in the open and close direction of the second grasping piece 14. When the first grasping piece 13 varies in its thickness in the open and close direction of the second grasping piece 14, the first grasping piece 13 varies in its bent amount in the close direction of the second grasping piece 14. For example, when the thickness of the first grasping piece 13 in the open and close direction of the second grasping piece 14 is a first thickness (indicated by the solid line in FIG. 6), the amount of bent of the first grasping piece 13 in the close direction of the second grasping piece 14 is a first amount of bent. When the thickness of the first grasping piece 13 in the open and close direction of the second grasping piece 14 is a second thickness (indicated by the broken line in FIG. 6) that is larger than the first thickness, the amount of bent of the first grasping piece 13 in the close direction of the second grasping piece 14 is a second amount of bent that is smaller than the first amount of bent.

For this reason, when the thickness of the first grasping piece 13 in the open and close direction of the second grasping piece 14 is a second thickness, the grasping force applied to the treatment target to be grasped between the first and second grasping pieces 13 and 14 becomes larger than that in the case where the thickness of the first grasping piece 13 in the open and close direction of the second grasping piece 14 is the first thickness. For example, the grasping force to grasp a blood vessel between the first and second grasping pieces 13 and 14 corresponds to a first grasping force when the thickness of the first grasping piece 13 in the open and close direction of the second grasping piece 14 is the first thickness, and the grasping force to grasp a blood vessel between the first and second grasping pieces 13 and 14 corresponds to a second grasping force that is larger than the first grasping force when the thickness of the first grasping piece 13 in the open and close direction of the second grasping piece 14 is the second thickness. As described above, in the present example, the first grasping piece 13 corresponds to the grasping force adjustment unit 41, and the driving member 42 or the selection unit 44 move the first grasping piece 13 in the axial rotation direction of the longitudinal axis C relative to the second grasping piece 14 to allow the grasping force applied to the treatment target to vary.

In another embodiment, the housing 4 may include, as the grasping force adjustment unit 41 (see FIG. 2), a ratchet (not shown) that has a plurality of groove portions (not shown) and a claw portion (not shown) extending to the groove portions of the ratchet from the handle 12. In this embodiment, the groove portions in which the claw portion is fit when the handle 12 operates to close relative to the grip 11, are formed along the longitudinal direction in the interior of the housing 4. When the handle 12 closes relative to the grip 11, the handle 12 moves to the proximal side along the longitudinal direction. In this instance, the claw portion is fit into one of the groove portions. When the handle 12 operates to close further relative to the grip 11 from this state, it moves to the proximal side further along the longitudinal direction. In this instance, the claw portion is fit into another one of the groove portions. In other words, when the handle 12 closes relative to the grip 11, a groove portion in which the claw portion is fit is changed to another by selecting a position to which the handle 12 moves.

In the present embodiment, the claw portion corresponds to the grasping force adjustment unit 41. If a groove portion in which the claw portion is fit when the handle 12 closes relative to the grip 11 is changed to another, the movement amount (stroke) by which the handle 12 moves when the handle 12 closes relative to the grip 11 varies. If the movement amount (stroke) by which the handle 12 moves when the handle 12 closes relative to the grip 11 varies, the movement amount by which the slide member 18 coupled to the handle 12 moves in the longitudinal direction relative to the movable member 17 varies. If the movement amount by which the slide member 18 moves relative to the movable member 17 varies, the displacement amount (contraction amount) of the coil spring 20 varies. As described above, the grasping force applied to a treatment target is determined in accordance with the displacement amount (contraction amount) of the coil spring 20. The grasping force applied to a treatment target can thus be varied by changing a groove portion in which the claw portion is fit. For example, when the claw portion of the handle 12 is fit in a first groove portion that is one of the groove portions, the movement amount by which the handle 12 operates to close corresponds to a first movement amount. Accordingly, the coil spring 20 contracts by displacement amount x1 from the reference state. Elastic force k0(x0+x1) is thus exerted on the movable member 17 from the coil spring 20, and the grasping force to grasp a blood vessel between the grasping pieces 13 and 14 is a first grasping force. When the claw portion of the handle 12 is fit in a second groove portion of the groove portions, which is located closer to the proximal side than the first groove portion, the movement amount by which the handle 12 operates to close corresponds to a second movement amount that is larger than the first movement amount. Accordingly, the coil spring 20 contracts by displacement amount x2, which is larger than displacement amount x1, from the reference state. Elastic force k0(x0+x2), which is larger than elastic force k0(x0+x1), is thus exerted on the movable member 17 from the coil spring 20, and the grasping force to grasp a blood vessel between the grasping pieces 13 and 14 is a second grasping force that is larger than the first grasping force. As described above, in the present example, the grasping force applied to the treatment target is varied by changing a groove portion in which the claw portion corresponding to the grasping force adjustment unit 41 is changed to another by operating the handle 12 serving as the selection unit 44.

As has been described in each of the exemplary embodiments, the grasping force adjustment unit has only to be configured to vary the grasping force to be applied to a treatment target (blood vessel) in accordance with an actuation state.

Next, the detector 43 will be described. The detector 43 detects information (parameter) about a blood vessel to be grasped between the grasping pieces 13 and 14. When a blood vessel is grasped between the grasping pieces 13 and 14, the blood vessel grasped between the grasping pieces 13 and 14 is contracted to some extent in the open and close direction of the end effector 6. FIG. 7 is a view showing the end effector 6 and a blood vessel M which is to be grasped between the grasping pieces 13 and 14 and which is contracted to some extent in the open and close direction of the end effector 6. As shown in FIG. 7, when the blood vessel M to be grasped is contracted to some extent in the open and close direction of the end effector 6, the upper and lower inner walls of the blood vessel M are brought into close contact with each other. Thus, the dimension H of the blood vessel M in the open and close direction of the end effector 6 when the blood vessel M to be grasped is contracted to some extent in the open and close direction of the end effector 6, is substantially proportionate to the wall thickness T of the blood vessel. When the grasped blood vessel M is contracted to some extent in the open and close direction of the end effector 6, the angle θ of the second grasping piece 14 to the first grasping piece 13 is proportionate to the dimension H of the blood vessel M grasped between the first and second grasping pieces 13 and 14 in the open and close direction of the end effector 6. Therefore, when the blood vessel M to be grasped is contracted to some extent in the open and close direction of the end effector 6, the angle θ of the second grasping piece 14 to the first grasping piece 13 is substantially proportionate to the wall thickness T of the blood vessel M.

Figure 8:
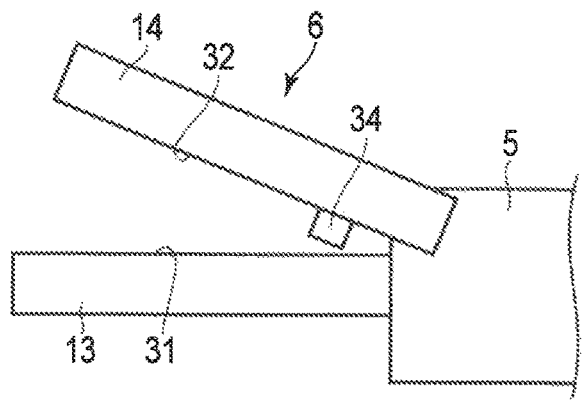
FIG. 8 is a schematic view showing a configuration of the end effector according to an exemplary embodiment.

In a certain example, a pressure sensor 34 is provided as the detector 43 at a proximal portion of the second opposing surface 32. FIG. 8 is a view showing the end effector 6 according to a certain example. As shown in FIG. 8, in the present example, the pressure sensor 34 protrudes in the close direction of the second grasping piece 14 on the second opposing surface 32. The pressure sensor 34 is electrically connected to the processor 47 of the energy controller 3 via an electrical circuit (not shown) which is formed in the interior of the energy treatment instrument 2. When the pressure sensor 34 abuts on the first opposing surface 31, the pressure sensor 34 receives pressure force from the first opposing surface 31. Thus, when the pressure sensor 34 abuts on the first opposing surface 31, pressure P received by the pressure sensor 34 becomes higher than that in the case where the pressure sensor 34 does not abut on the first opposing surface 31.

Figure 9:
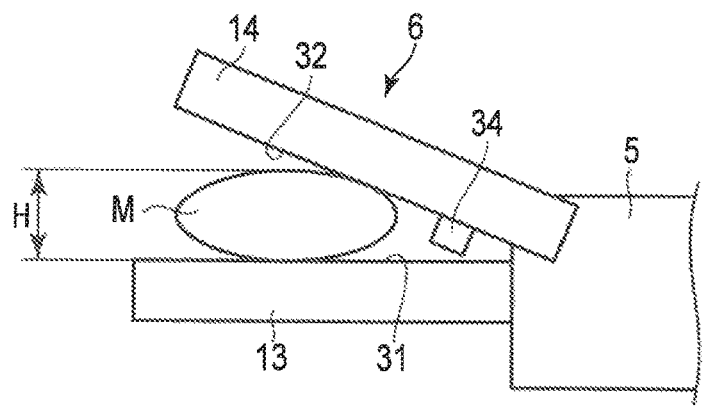
FIG. 9 is a schematic view showing the end effector according to an exemplary embodiment, by which a blood vessel whose wall thickness is larger than a predetermined thickness is grasped.
Figure 10:
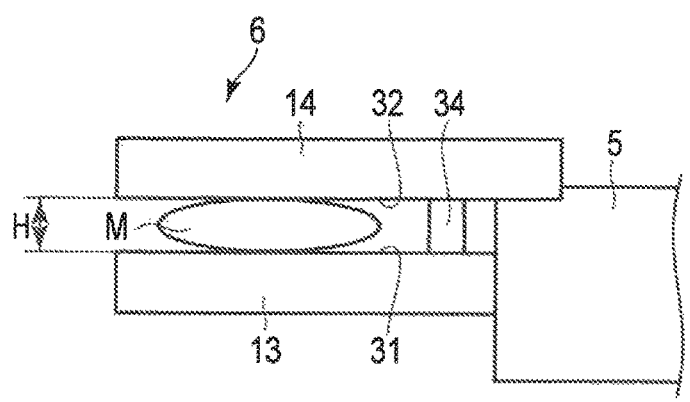
FIG. 10 is a schematic view showing the end effector according to an exemplary embodiment, by which a blood vessel whose wall thickness is smaller than a predetermined thickness is grasped.

The detector 43 is used with the blood vessel M grasped between the grasping pieces 13 and 14 contracted to some extent in the open and close direction of the end effector 6. FIGS. 9 and 10 are views each showing the end effector 6 and the blood vessel M contracted to some extent in the open and close direction of the end effector 6. The blood vessels M shown in FIGS. 9 and 10 are different in wall thickness T. As shown in FIG. 9, for example, when the wall thickness T of the blood vessel M to be grasped is larger than a predetermined thickness Tth, the dimension H increases with the blood vessel M contracted to some extent in the open and close direction of the end effector 6. Thus, the pressure sensor 34 is not brought into contact with the first opposing surface 31, but the pressure received by the pressure sensor 34 decreases. A sensing signal indicating a sensing result in the pressure sensor 34 is input to the setting unit 51 of the processor 47. In this instance, information of the pressure received by the pressure sensor 34 is input to the setting unit 51 as information regarding the blood vessel M. In the state shown in FIG. 9, based on the sensing signal from the pressure sensor 34, the setting unit 51 determines that the pressure P received by the pressure sensor 34 is smaller than a threshold value Pth. As described above, when the wall thickness T of the blood vessel M is large, the dimension H increases with the blood vessel M contracted to some extent in the open and close direction of the end effector 6, and the pressure P received by the pressure sensor 34 decreases. When the setting unit 51 thus determines that the pressure P is smaller than the threshold value Pth, it determines that the wall thickness T of the blood vessel M to be grasped is larger than the predetermined thickness Tth. In this instance, the setting unit 51 may determine the blood vessel M to be grasped as a blood vessel of a systemic circulatory system with a relatively large wall thickness T.

Furthermore, as shown in FIG. 10, for example, when the wall thickness T of the blood vessel M to be grasped is less than the predetermined thickness Tth, the dimension H decreases with the blood vessel M contracted to some extent in the open and close direction of the end effector 6. Accordingly, the pressure sensor 34 abuts on the first opposing surface 31 and the pressure received by the pressure sensor 34 increases. In the state shown in FIG. 10, too, a sensing signal indicating a sensing result (information regarding the blood vessel M) in the pressure sensor 34 is input to the setting unit 51. In the state shown in FIG. 10, based on the sensing signal from the pressure sensor 34, the setting unit 51 determines that the pressure P received by the pressure sensor 34 is equal to or larger than the threshold value Pth. As described above, when the wall thickness T of the blood vessel M is small, the dimension H decreases with the blood vessel M contracted to some extent in the open and close direction of the end effector 6, and the pressure P received by the pressure sensor 34 increases. When the setting unit 51 thus determines that the pressure P is equal to or larger than the threshold value Pth, it determines that the wall thickness T of the blood vessel M to be grasped is equal to or smaller than the predetermined thickness Tth. In this instance, the setting unit 51 may determine the blood vessel M to be grasped as a blood vessel of a pulmonary circulatory system with a relatively small wall thickness T.

As described above, in the present example, the pressure sensor 34 senses the pressure P received by the pressure sensor 34 as information (parameter) regarding the blood vessel M. Furthermore, based on the sensing signal from the pressure sensor 34, the setting unit 51 can obtain information regarding the wall thickness T of the blood vessel M. Then, based on the information regarding the blood vessel M (information of the pressure received by the pressure sensor 34), which is input to the setting unit 51, the setting unit 51 sets information regarding the wall thickness T such as whether the wall thickness T of the blood vessel M is larger than the predetermined thickness Tth, or a type of the blood vessel M (a systemic circulatory system or a pulmonary circulatory system). In other words, in the present embodiment, the pressure sensor 34 corresponds to the detector 43 to sense information regarding the blood vessel M to be grasped.

Note in the present example that only one pressure sensor 34 is provided on the second opposing surface 32, which is, however, not restrictive. For example, the pressure sensor 34 can be provided at each of the proximal and distal portions of the second opposing surface 32. The pressure sensor 34 can also be provided at the proximal portion of the first opposing surface 31. In other words, one or more pressure sensors 34 have only to be provided on at least one of the first and second opposing surfaces 31 and 32.

Figure 11:
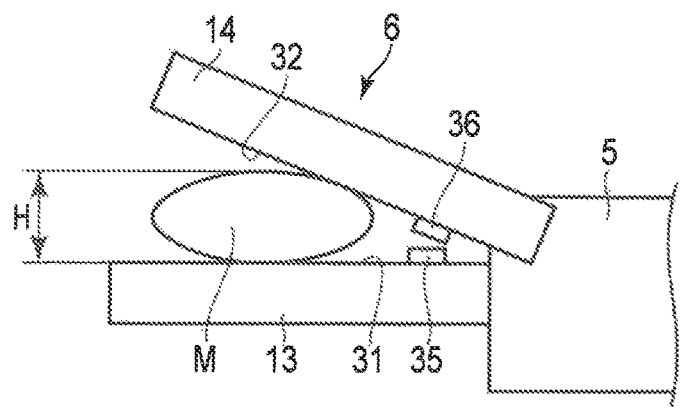
FIG. 11 is a schematic view showing an end effector according to an exemplary embodiment, by which a blood vessel whose wall thickness is larger than a predetermined thickness is grasped.
Figure 12:
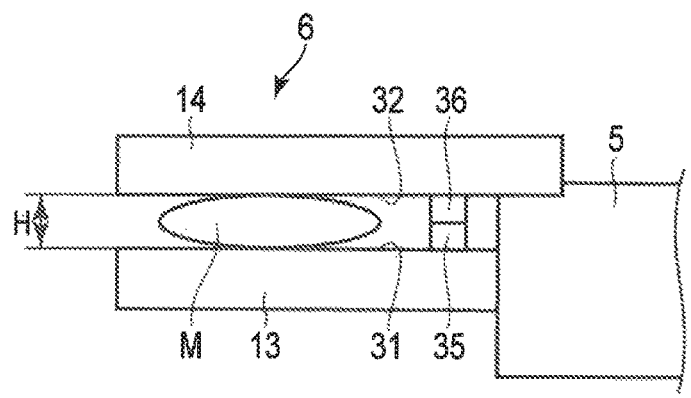
FIG. 12 is a schematic view showing the end effector according to an exemplary embodiment, by which a blood vessel whose wall thickness is smaller than a predetermined thickness is grasped.

As another exemplary embodiment, conductive members 35 and 36 can be provided as the detector 43 in place of the pressure sensor 34. FIGS. 11 and 12 are views each showing an end effector 6 and a blood vessel M contracted to some extent in the open and close direction of the end effector 6 in the present embodiment. The blood vessels M shown in FIGS. 11 and 12 are different in wall thickness T. As shown in FIGS. 11 and 12, in the present embodiment, the first conductive member 35 is provided at the proximal portion of the first opposing surface 31 to protrude in the close direction of the first grasping piece 13. The second conductive member 36 is opposed to the first conductive member 35 and provided at the proximal portion of the second opposing surface 32 to protrude in the close direction of the second grasping piece 14. The first and second conductive members 35 and 36 are supplied with electrical energy, which is different from electrical energy to be converted into driving power and treatment energy, from the power supply unit 46 of the energy controller 3. As shown in FIG. 11, when the wall thickness T of the blood vessel M to be grasped is relatively large (e.g. when it is larger than the predetermined thickness Tth), the foregoing dimension H increases and thus the first and second conductive members 35 and 36 are not brought into contact with each other. For this reason, no current flows through an electrical circuit that is routed through the first conductive member 35, second conductive member 36 and power supply unit 46. For example, based on that no current flows through the electrical circuit as described above, the setting unit 51 determines that the wall thickness T of the blood vessel M is larger than the predetermined thickness Tth or determines that the blood vessel M to be grasped is a blood vessel of a systemic circulatory system with a relatively large wall thickness T. On the other hand, when the wall thickness T of the blood vessel M is relatively small (e.g. when it is equal to or smaller than the predetermined thickness Tth), the dimension H decreases and thus the first and second conductive members 35 and 36 are brought into contact with each other. For this reason, current flows through the electrical circuit that is routed through the first conductive member 35, second conductive member 36 and power supply unit 46. For example, based on that current flows through the electrical circuit as described above, the setting unit 51 determines that the wall thickness T of the blood vessel M is equal to or smaller than the predetermined thickness Tth or determines that the blood vessel M to be grasped is a blood vessel of a pulmonary circulatory system with a relatively small wall thickness T. As described above, in the present example, the first and second conductive members 35 and 36 of the detector 43 detect, as information regarding the blood vessel M, whether current flows through the electrical circuit that is routed through the first conductive member 35, second conductive member 36 and power supply unit 46. Based on the detected information regarding the blood vessel M, the setting unit 51 sets information regarding the wall thickness T such as whether the wall thickness T of the blood vessel M is larger than the predetermined thickness Tth, or a type of the blood vessel M (a systemic circulatory system or a pulmonary circulatory system).

Figure 13:
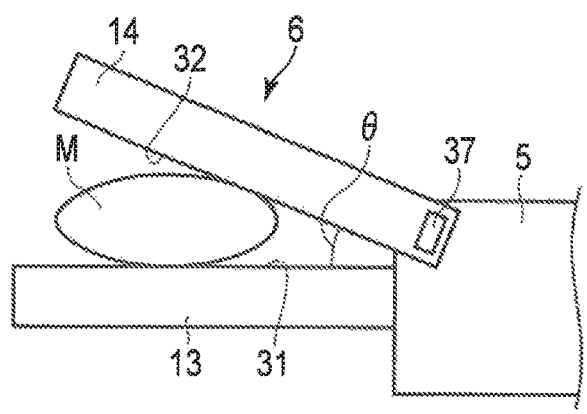
FIG. 13 is a schematic view schematically showing a configuration of an end effector according to an exemplary embodiment.

According to another exemplary embodiment, an angle sensor 37 can be provided as the detector 43, as shown in FIG. 13. FIG. 13 is a view showing an end effector 6 and a blood vessel M according to the present embodiment, with the blood vessel M, which is grasped between the grasping pieces 13 and 14, contracted to some extent in the open and close direction of the end effector 6. As shown in FIG. 13, in the present embodiment, the angle sensor 37 is provided in a coupling section between the second grasping piece 14 and the sheath 5. The angle sensor 37 senses angle θ between the first grasping piece 13 and the second grasping piece 14. As the angle sensor 37, for example, an encoder or a potentiometer is used. The angle sensor 37 is electrically connected to the processor 47 of the energy controller 3 via a signal path (not shown) formed in the interior of the energy treatment instrument 2.

The angle sensor 37 of the detector 43 is used when the blood vessel M grasped between the grasping pieces 13 and 14 is contracted to some extent in the open and close direction of the end effector 6. For example, when the wall thickness T of the blood vessel M to be grasped is larger than the predetermined thickness Tth, the angle θ between the first and second grasping pieces 13 and 14 increases. A sensing signal indicating a sensing result of the angle sensor 37 is input to the setting unit 51 of the processor 47. In this instance, the angle θ between the first and second grasping pieces 13 and 14 is input to the setting unit 51 as information regarding the blood vessel M. Based on the sensing signal from the angle sensor 37, the setting unit 51 determines that the angle θ between the first and second grasping pieces 13 and 14 is larger than a threshold value θth. As described above, when the wall thickness T of the blood vessel M is large, the angle θ between the first and second grasping pieces 13 and 14 increases. When the setting unit 51 thus determines that the angle θ between the first and second grasping pieces 13 and 14 is larger than the threshold value θth, it determines that the wall thickness T of the blood vessel M to be grasped is larger than the predetermined thickness Tth. In this instance, the setting unit 51 may determine the blood vessel M to be grasped as a blood vessel of a systemic circulatory system with a relatively large wall thickness T.

Furthermore, for example, when the wall thickness T of the blood vessel M to be grasped is equal to or smaller than the predetermined thickness Tth, the angle θ between the first grasping piece 13 and the second grasping piece decreases. In this instance, a sensing signal indicating a sensing result of the angle sensor 37 (information regarding the blood vessel M) is input to the setting unit 51. Based on the sensing signal from the angle sensor 37, the setting unit 51 determines that the angle θ between the first and second grasping pieces 13 and 14 is equal to or smaller than the threshold value θth. As described above, when the wall thickness T of the blood vessel M is small, the angle θ between the first and second grasping pieces 13 and 14 decreases. When the setting unit 51 thus determines that the angle θ between the first and second grasping pieces 13 and 14 is equal to or smaller than the threshold value θth, it determines that the wall thickness T of the blood vessel M to be grasped is equal to or smaller than the predetermined thickness Tth. In this instance, the setting unit 51 may determine the blood vessel M to be grasped as a blood vessel of a pulmonary circulatory system with a relatively small wall thickness T.

As described above, in the present embodiment, the angle sensor 34 senses the angle θ between the first and second grasping pieces 13 and 14 as information (parameter) regarding the blood vessel M. Furthermore, based on the sensing signal from the angle sensor 37, the setting unit 51 can obtain information regarding the wall thickness T of the blood vessel M. Then, based on the information regarding the blood vessel M (information of the angle θ between the first and second grasping pieces 13 and 14), which is input to the setting unit 51, the setting unit 51 sets information regarding the wall thickness T such as whether the wall thickness T of the blood vessel M is larger than the predetermined thickness Tth, or a type of the blood vessel M (a systemic circulatory system or a pulmonary circulatory system). In other words, in the present embodiment, the angle sensor 37 corresponds to the detector 43 to sense information regarding the blood vessel M to be grasped.

Figure 14:
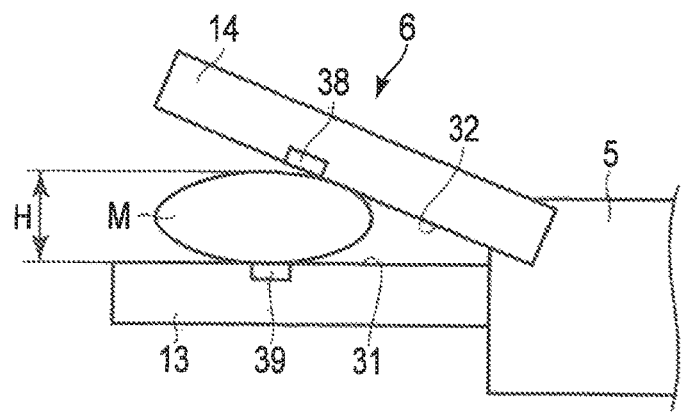
FIG. 14 is a schematic view schematically showing a configuration of an end effector according to an exemplary embodiment.

According to another exemplary embodiment, a light-receiving element 39 can be provided as the detector 43, as shown in FIG. 14. FIG. 14 is a view showing an end effector 6 and a blood vessel M according to the present embodiment, with the blood vessel M, which is grasped between the grasping pieces 13 and 14, contracted to some extent in the open and close direction of the end effector 6. As shown in FIG. 14, in the present embodiment, a light-emitting element 38 such as an LED is provided on the second opposing surface 32. Furthermore, a light-receiving element 39 such as a PD is provided on the first opposing surface 31. The light-receiving element 39 is electrically connected to the processor 47 of the energy controller 3 via a signal path (not shown) formed in the interior of the energy treatment instrument 2. Upon receiving electrical energy, which is different from electrical energy to be converted into driving power and treatment energy, from the energy controller 3, the light-emitting element 38 emits light to the light-receiving element 39. The light-receiving element 39 detects an amount of light (light intensity) Q incident upon the light-receiving element 39.

The detector 43 is used with the blood vessel M grasped between the grasping pieces 13 and 14 contracted to some extent in the open and close direction of the end effector 6. In this instance, the light-emitting element 38 emits light to the blood vessel M and the light-receiving element 39. Part of the light emitted to the blood vessel M is reflected or absorbed by blood vessel tissue in the interior of the blood vessel M. Of the light emitted to the blood vessel M, light (transmitted light) that is neither reflected nor absorbed by the blood vessel tissue enters the light-receiving element 39. Then, the light-receiving element 39 detects the light amount Q of transmitted light. For example, when the wall thickness T of the blood vessel M to be grasped is larger than a predetermined thickness Tth, the dimension H increases with the blood vessel M contracted to some extent in the open and close direction of the end effector 6. Accordingly, of the light emitted to the blood vessel M, light reflected or absorbed by the blood vessel tissue increases in amount. The amount of light reflected or absorbed by the blood vessel tissue increases, the light amount Q of transmitted light that enters the light-receiving element 39 decreases. A detection signal indicating a detection result in the light-receiving element 39 is input to the setting unit 51 of the processor 47. In this instance, information of the light amount Q of transmitted light that enters the light-receiving element 39 as information regarding the blood vessel M is input to the setting unit 51. Based upon the detection signal from the light-receiving element 39, the setting unit 51 determines that the light amount Q of transmitted light that enters the light-receiving element 39 is smaller than a threshold value Qth. As described above, when the wall thickness T of the blood vessel M is large, the foregoing dimension H increases and the light amount Q of transmitted light that enters the light-receiving element 39 decreases. When the setting unit 51 thus determines that the light amount Q is smaller than the threshold value Qth, it determines that the wall thickness T of the blood vessel M to be grasped is larger than the predetermined thickness Tth. In this instance, the setting unit 51 may determine the blood vessel M to be grasped as a blood vessel of a systemic circulatory system with a relatively large wall thickness T.

For example, when the wall thickness T of the blood vessel M to be grasped is equal to or smaller than the predetermined thickness Tth, the dimension H decreases with the blood vessel M contracted to some extent in the open and close direction of the end effector 6. Accordingly, of the light emitted to the blood vessel M, light reflected or absorbed by the blood vessel tissue decreases in amount. When the amount of light reflected or absorbed by the blood vessel tissue decreases, the light amount Q of transmitted light that enters the light-receiving element 39 increases. A detection signal indicating a detection result in the light-receiving element 39 is input to the setting unit 51 of the processor 47. In this instance, information of the light amount Q of transmitted light that enters the light-receiving element 39 as information regarding the blood vessel M is input to the setting unit 51. Based upon the detection signal from the light-receiving element 39, the setting unit 51 determines that the light amount Q of transmitted light that enters the light-receiving element 39 is larger than the threshold value Qth. As described above, when the wall thickness T of the blood vessel M is small, the foregoing dimension H decreases and the light amount Q of transmitted light that enters the light-receiving element 39 increases. When the setting unit 51 thus determines that the light amount Q of transmitted light that enters the light-receiving element 39 is equal to or larger than the threshold value Qth, it determines that the wall thickness T of the blood vessel M to be grasped is equal to or smaller than the predetermined thickness Tth. In this instance, the setting unit 51 may determine the blood vessel M to be grasped as a blood vessel of a pulmonary circulatory system with a relatively small wall thickness T.

As described above, in the present example, the light-receiving element 39 detects the light amount Q of transmitted light that enters the light-receiving element 39 as information (parameter) regarding the blood vessel M. Furthermore, based on the detection signal from the light-receiving element 39, the setting unit 51 can obtain information regarding the wall thickness T of the blood vessel M. Then, based on the information regarding the blood vessel M (information of the light amount Q of transmitted light that enters the light-receiving element 39), which is input to the setting unit 51, the setting unit 51 sets information regarding the wall thickness T such as whether the wall thickness T of the blood vessel M is larger than the predetermined thickness Tth, or a type of the blood vessel M (a systemic circulatory system or a pulmonary circulatory system). In other words, in the present embodiment, the light-receiving element 39 corresponds to the detector 43 to detect information regarding the blood vessel M to be grasped.

Figure 15:
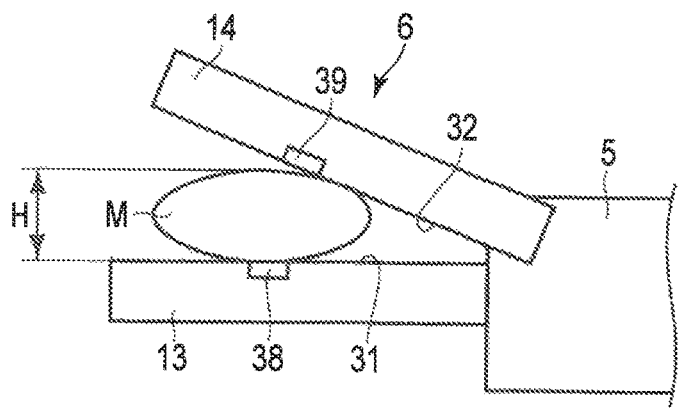
FIG. 15 is a schematic view schematically showing a configuration of an end effector according to an exemplary embodiment.
Figure 16:
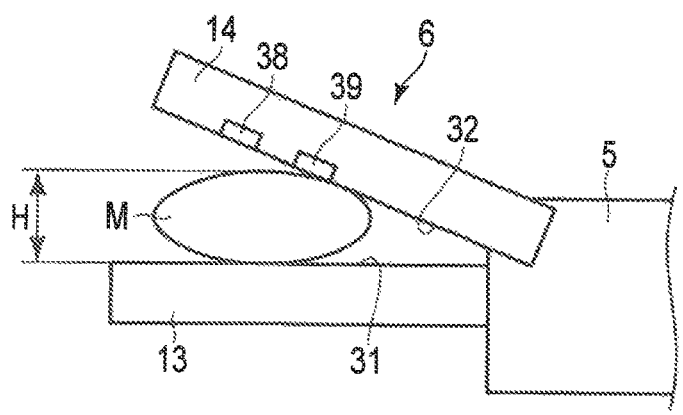
FIG. 16 is a schematic view schematically showing a configuration of an end effector according to an exemplary embodiment.

Note that in the present embodiment, the light-emitting element 38 is provided on the second opposing surface 32 and the light-receiving element 39 is provided on the first opposing surface 31, which is, however, not restrictive. For example, another exemplary embodiment is shown in FIG. 15, in which the light-emitting element 38 can be provided on the first opposing surface 31 and the light-receiving element 39 can be provided on the second opposing surface 32. Furthermore, in yet another embodiment shown in FIG. 16, both the light-emitting element 38 and the light-receiving element 39 can be provided on the second opposing surface 32. In this case, the light-receiving element 39 detects the amount of light that is reflected by the first opposing surface 31 and then enters the light-receiving element 39. Note that both the light-emitting element 38 and the light-receiving element 39 can be provided on the first opposing surface 31.

Note that the information regarding the blood vessel used in the present embodiment is not limited to the amount of light. For example, in place of light, ultrasound can be provided in another embodiment. In this case, ultrasonic diagnostic equipment (not shown) is provided as the detector 43. In place of the light-emitting element 38 and the light-receiving elements 39, an ultrasonic emission unit (not shown) and an ultrasonic reception unit (not shown) are provided. In the present embodiment, the ultrasonic emission unit emits ultrasound to the blood vessel M and the ultrasonic reception unit detects ultrasound that is transmitted through the blood vessel M. Then, information of the emitted ultrasound and information of the detected ultrasound are input to the setting unit 51 of the processor 47. In this instance, information of ultrasound to be emitted and information of ultrasound to be detected as information regarding the blood vessel M are input to the setting unit 51. The setting unit 51 visualizes the interior of the blood vessel M using a time difference between time when ultrasound is emitted and time when ultrasound is detected. Then, based on an image of the visualized interior of the blood vessel M, the setting unit 51 determines that the wall thickness T of the blood vessel M to be grasped is larger than the predetermined thickness Tth (or equal to or smaller than the predetermined thickness Tth). In this instance, the setting unit 51 may determine the blood vessel M to be grasped as a blood vessel of a systemic circulatory system with a relatively large wall thickness T (or a blood vessel of a pulmonary circulatory system with a relatively small wall thickness T).

In another exemplary embodiment, the detector 43 can be provided in the interior of the housing 4 and configured to detect a displacement amount (contraction amount) x by which the coil spring 20 is contracted from the reference state, with the blood vessel M to be grasped contracted to some extent in the open and close direction of the end effector 6. In this case, a detection signal indicating a detection result in the detector 43 is input to the setting unit 51 of the processor 47. In this instance, the foregoing displacement amount (contraction amount) x by which the coil spring 20 is contracted from the reference state is input to the setting unit 51 as information regarding the blood vessel M. The displacement amount (contraction amount) x by which the coil spring 20 is contracted from the reference state varies with the foregoing dimension H with the blood vessel M to be grasped contracted to some extent in the open and close direction of the end effector 6. Here, the dimension H is substantially proportionate to the wall thickness T of the blood vessel M. Then, based on the displacement amount (contraction amount) x by which the coil spring 20 is contracted from the reference state, the setting unit 51 determines that the wall thickness T of the blood vessel M to be grasped is larger than the predetermined thickness Tth (or equal to or smaller than the predetermined thickness Tth). In this instance, the setting unit 51 may determine the blood vessel M to be grasped as a blood vessel of a systemic circulatory system with a relatively large wall thickness T (or a blood vessel of a pulmonary circulatory system with a relatively small wall thickness T).

In another exemplary embodiment, an electrical circuit (not shown) that is routed through the power supply unit 46 and electrodes (not shown) provided in their respective first and second grasping pieces 13 and 14, can be provide as the detector 43. In the present embodiment, the electrodes are provided in their respective first and second grasping pieces 13 and 14 and supplied with electrical energy (high-frequency power) from the power supply unit 46 of the energy controller 3. When the electrodes are supplied with electrical energy with a blood vessel grasped between the first and second grasping pieces 13 and 14, high-frequency current flows through the blood vessel between the electrodes. When high-frequency current is used as treatment energy, high-frequency current is supplied to a blood vessel to be grasped as treatment energy through the first opposing surface 31 of the first grasping piece 13 and the second opposing surface 32 of the second grasping piece 14, which are energy application sections. When high-frequency current is not supplied to the blood vessel as treatment energy, high-frequency current flows through the blood vessel to such a degree that the blood vessel to be grasped is not degenerated. Then, the foregoing electrical circuit detects the high-frequency current flowing through the blood vessel.

The detector 43 is used with the blood vessel M grasped between the grasping pieces 13 and 14 contracted to some extent in the open and close direction of the end effector 6. In this instance, an electrical circuit is formed to be routed through the electrodes provided in their respective grasping pieces 13 and 14, the blood vessel M and the power supply unit 46. When the power supply unit 46 supplies electrical energy (high-frequency power) to the foregoing electrical circuit, high-frequency current flows into the electrical circuit through the blood vessel M. The current flowing into the electrical circuit through the blood vessel M is input to the setting unit 51 as information regarding the blood vessel. For example, when the wall thickness T of the blood vessel M to be grasped is larger than the predetermined thickness Tth, the dimension H increases with the blood vessel M contracted to some extent in the open and close direction of the end effector 6. Accordingly, water contained in the section of the blood vessel M in the open and close direction of the end effector 6 increases. It is known that the electrical resistance of water is low. The more the water contained in the section of the blood vessel M in the open and close direction of the end effector 6, the lower the impedance Z (electrical resistance) of the blood vessel M. When the water contained in the section of the blood vessel M in the open and close direction of the end effector 6 increases, the impedance Z (electrical resistance) of the blood vessel M lowers. Based on a detection result in the detector 43 (high-frequency current flowing into the electrical circuit through the blood vessel M), the setting unit 51 calculates impedance Z of the blood vessel M and determines that the impedance Z of the blood vessel M is smaller than a threshold value Zth based on the calculation result. As described above, when the wall thickness T of the blood vessel M is large, the impedance Z of the blood vessel M decreases with the blood vessel M contracted to some extent in the open and close direction of the end effector 6. Thus, when the setting unit 51 determines that the impedance Z is smaller than the threshold value Zth, it determines that the wall thickness T of the blood vessel M to be grasped is larger than the predetermined thickness Tth. In this instance, the setting unit 51 may determine the blood vessel M to be grasped as a blood vessel of a systemic circulatory system with a relatively large wall thickness T.

Furthermore, for example, when the wall thickness T of the blood vessel M to be grasped is equal to or smaller than the predetermined thickness Tth, the foregoing dimension H decreases. Accordingly, water contained in the section of the blood vessel M in the open and close direction of the end effector 6 decreases. As described above, it is known that the electrical resistance of water is low. The less the water contained in the section of the blood vessel M in the open and close direction of the end effector 6, the higher the impedance Z (electrical resistance) of the blood vessel M. When the water contained in the section of the blood vessel M in the open and close direction of the end effector 6 decreases, the impedance Z (electrical resistance) of the blood vessel M heightens. Based on a detection result in the detector 43 (characteristics of current flowing through the blood vessel M), the setting unit 51 calculates impedance Z of the blood vessel M and determines that the impedance Z of the blood vessel M is equal to or higher than the threshold value Zth based on the calculation result. As described above, when the wall thickness T of the blood vessel M is small, the impedance Z of the blood vessel M increases with the blood vessel M contracted to some extent in the open and close direction of the end effector 6. Thus, when the setting unit 51 determines that the impedance Z is equal to or higher than the threshold value Zth, it determines that the wall thickness T of the blood vessel M to be grasped is equal to or smaller than the predetermined thickness Tth. In this instance, the setting unit 51 may determine the blood vessel M to be grasped as a blood vessel of a pulmonary circulatory system with a relatively small wall thickness T.

As described above, in the present example, the characteristics of high-frequency current flowing through the blood vessel M to be grasped are detected as information (parameter) regarding the blood vessel M, using an electrical circuit that is routed through the power supply unit 46 and the electrodes provided in their respective first and second grasping pieces 13 and 14. Furthermore, based on a detection signal indicating the foregoing characteristics of high-frequency current, the setting unit 51 can obtain information regarding the wall thickness T of the blood vessel M. Then, based on the information regarding the blood vessel M (characteristics of high-frequency current flowing through the blood vessel M to be grasped), which is input to the setting unit 51, the setting unit 51 sets information regarding the wall thickness T such as whether the wall thickness T of the blood vessel M is larger than the predetermined thickness Tth, or a type of the blood vessel M (a systemic circulatory system or a pulmonary circulatory system). In other words, in the present embodiment, the electrodes provided in their respective first and second grasping pieces 13 and 14 correspond to the detector 43 to detect information regarding the blood vessel M to be grasped.

Next, functions and advantageous effects of the energy treatment instrument 2 and the energy surgical instrument 1 according to the present embodiment will be described. The energy surgical instrument 1 is generally used for treatment to cut a blood vessel open and simultaneously seal (coagulate) it. FIG. 17 is a view showing a structure of a heart 100 and its neighborhood. As shown in FIG. 17, the heart 100 includes a left atrium 101, a left ventricle 102, a right atrium 103 and a right ventricle 104. The pulmonary vein 105 extends from the left atrium 101 and the main artery 106 extends from the left ventricle 102. The main vein 107 extends from the right atrium 103 and the pulmonary artery 108 extends from the right ventricle 104. Here, a circulatory pathway that guides blood from the left ventricle 102 to the whole body through the main artery 106 and returns the blood from the whole body to the right atrium 103 through the main vein 107 is referred to as systemic circulation. A circulatory pathway that guides blood from the right ventricle 104 to the lungs through the pulmonary artery 108 and returns the blood from the lungs to the left atrium 101 through the pulmonary vein 105 is referred to as pulmonary circulation.

To treat a blood vessel, the end effector 6 is inserted into a chest cavity and moved until the blood vessel is located between the first and second grasping pieces 13 and 14. Then, the handle 12 is closed relative to the grip 11 with the blood vessel to be treated between the first and second grasping pieces 13 and 14. When the handle 12 is closed relative to the grip 11, the blood vessel is contracted to some extent in the open and close direction of the end effector 6. Then, the first and second grasping pieces 13 and 14 are closed relative to each other to grasp the blood vessel. When the blood vessel is grasped between the first and second grasping pieces 13 and 14, the running direction of the blood vessel crosses the longitudinal direction and the open and close direction of each of the first and second grasping pieces 13 and 14. If an input operation is performed by the operational button 33 when the blood vessel is grasped between the first and second grasping pieces 13 and 14, at least one of ultrasonic vibration, high-frequency current, heat and the like is applied to the blood vessel to cut the blood vessel open and simultaneously seal (coagulate) it as described above.

Here, the wall thickness T of blood vessels of pulmonary circulation is considered to be smaller than that of blood vessels of systemic circulation. Thus, the number of biopolymers gelatinized in sealing treatment (bonding treatment) on the section of a blood vessel of pulmonary circulation, which is perpendicular to the extending direction of the biopolymers is smaller than that on the section of a blood vessel of systemic circulation, the sections having the same diameter. Therefore, when a blood vessel of pulmonary circulation and a blood vessel of systemic circulation are treated, if the same grasping force is exerted on both the blood vessels, it is likely to have an influence upon the treatment performance.

When a blood vessel is treated with the energy treatment instrument 2 and the energy surgical instrument 1 according to the present embodiment, information regarding the blood vessel to be grasped between the grasping pieces 13 and 14 is detected by the detector 43 as described above. Then, the information regarding the wall thickness detected by the detector 43 is input to the setting unit 51. Based on the information regarding the blood vessel input to the setting unit 51, the setting unit 51 sets information regarding the wall thickness T of the blood vessel to be grasped. Then, in accordance with the information regarding the wall thickness T set by the setting unit 51, the drive controller 52 determines a parameter regarding the grasping force exerted on a treatment target to be grasped between the grasping pieces 13 and 14.

When the wall thickness T is larger than the predetermined thickness Tth, or when the blood vessel to be grasped is a blood vessel of a systemic circulatory system, the drive controller 52 determines that a first grasping force is exerted on the blood vessel to be grasped between the grasping pieces. Based on the determination, the drive controller 52 controls driving power to be applied to the driving member 42 from the driving power output unit 50. Accordingly, the driving of the driving member 42 is controlled, as is the actuation of the grasping force adjustment unit 41. When the actuation of the grasping force adjustment unit 41 is controlled, the first grasping force is exerted on the blood vessel grasped between the grasping pieces 13 and 14.

When the wall thickness T is equal to or smaller than the predetermined thickness Tth, or when the blood vessel to be grasped is a blood vessel of a pulmonary circulatory system, the drive controller 52 determines to exert the second grasping force, which is larger than the first grasping force, on a treatment target to be grasped between the grasping pieces 13 and 14. Based on the determination, the drive controller 52 controls the driving power to be supplied to the driving member 42 from the driving power output unit 50. Accordingly, the driving of the driving member 42 is controlled, as is the actuation of the grasping force adjustment unit 41. When the actuation of the grasping force adjustment unit 41 is controlled, the second grasping force is exerted on the blood vessel grasped between the grasping pieces 13 and 14.

As described above, when the grasping force adjustment unit 41 adjusts the grasping force to grasp a blood vessel between the first and second grasping pieces 13 and 14 to the first grasping force when the wall thickness T set by the setting unit 51 is larger than the predetermined thickness Tth, and adjusts the grasping force to grasp a blood vessel between the first and second grasping pieces 13 and 14 to the second grasping force, which is larger than the first grasping force, when the wall thickness T set by the setting unit 51 is equal to or smaller than the predetermined thickness Tth.

Note that, for example, the information regarding the wall thickness T of the blood vessel (information indicating whether the wall thickness T is larger than the predetermined thickness Tth and/or information indicating a type of the blood vessel) set by the setting unit 51 of the processor 47 can be notified to a surgeon by, e.g. a notification unit (not shown) provided in the energy controller 3 or the like. In this case, based on the notified information regarding the wall thickness T of the blood vessel, the surgeon manually operates the selection unit 44 (see FIG. 2) attached to, e.g. the housing 4 to adjust the actuation state of the grasping force adjustment unit 41. Accordingly, the grasping force exerted on the blood vessel between the grasping pieces 13 and 14 is adjusted. For example, when it is notified that the wall thickness T is larger than the predetermined thickness Tth, the selection unit 44 is operated to adjust the grasping force to grasp the blood vessel between the first and second grasping pieces 13 and 14 to the first grasping force. When it is notified that the wall thickness T is equal to or smaller than the predetermined thickness Tth, the selection unit 44 is operated to adjust the grasping force to grasp the blood vessel between the first and second grasping pieces 13 and 14 to the second grasping force which is larger than the first grasping force.

Furthermore, for example, the information input unit 53 provided in the energy controller 3 can be operated to input information regarding a blood vessel. In this case, the setting unit 51 sets information regarding the wall thickness T of the blood vessel to be grasped based on an input result in the information input unit 53 (information regarding the blood vessel input to the information input unit 53). Then, based on the set information regarding the wall thickness T of the blood vessel, the drive controller 52 controls the actuation of the grasping force adjustment unit 41 or the surgeon manually operates the selection unit 44 to adjust the grasping force exerted on the blood vessel between the grasping pieces 13 and 14.

Figure 19:
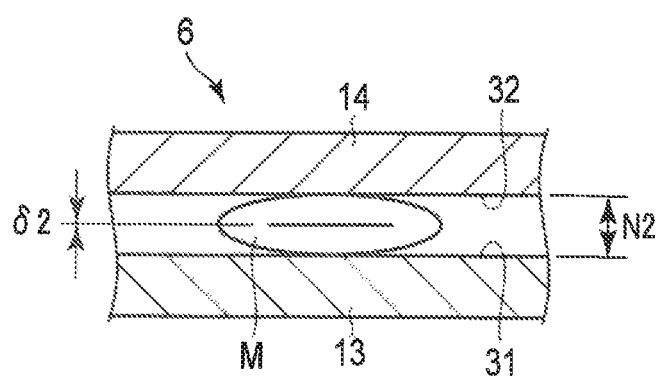
FIG. 19 is a schematic view showing the end effector according to an exemplary embodiment, by which a blood vessel is grasped with a second grasping force.

FIGS. 18 and 19 are sectional views showing the end effector 6 and the blood vessel M, which are substantially perpendicularly to the width direction of the end effector 6 when the first grasping force and the second grasping force are exerted on the blood vessel M grasped between the grasping pieces 13 and 14. As shown in FIG. 18, when the first grasping force is exerted on the blood vessel M, the upper and lower inner walls of the blood vessel M come close to each other and the distance between the upper and lower inner walls of the blood vessel M is a first distance 61.

On the other hand, as shown in FIG. 19, when the second grasping force, which is larger than the first grasping force, is exerted on the blood vessel M, the upper and lower inner walls of the blood vessel M further come close to each other and the distance between the upper and lower inner walls of the blood vessel M is a second distance 62 that is smaller than the first distance 61. The second distance 62 is zero or very close to zero. The second distance 62 is smaller than the first distance 61. Thus, when the second grasping force is exerted on the blood vessel M, the degree of adhesion between the upper and lower inner walls of the blood vessel M becomes higher than that in the case where the first grasping force is exerted on the blood vessel. When the second grasping force is exerted on the blood vessel M, the number of biopolymers gelatinized in a grasping region between the grasping pieces 13 and 14 becomes larger than that in the case where the first grasping force is exerted on the blood vessel. Since, therefore, even a blood vessel whose wall thickness T is small, such as a blood vessel of a pulmonary circulatory system, is grasped with a large grasping force (e.g. second grasping force), the degree of adhesion between the upper and lower inner walls of the blood vessel M is secured in sealing treatment, as is the number of biopolymers gelatinized in a grasping region between the grasping pieces 13 and 14 Thus, even in a blood vessel whose wall thickness T is small, sealing performance is secured in sealing treatment, and treatment performance is secured in treatment to cut a blood vessel open and simultaneously coagulate it.

In the present embodiment, therefore, the energy surgical instrument 1 can be provided which is suitable for treatment to seal (and simultaneously coagulate) a blood vessel whose wall thickness T is small such as a blood vessel of a pulmonary circulatory system. In the present embodiment, furthermore, the energy surgical instrument 1 can be provided which can exercise appropriate treatment performance even though blood vessels which differ in wall thickness T, such as a blood vessel of a pulmonary circulatory system and a blood vessel of a systemic circulatory system that differ in wall thickness T, are sealed.

If a blood vessel is sealed using high-frequency energy, the following additional advantageous effects are produced. When high-frequency energy is used for sealing treatment, electrodes (not shown) are provided in their respective first and second grasping pieces 13 and 14 and supplied with electrical energy (high-frequency power) from the power supply unit 46 of the energy controller 3. A high-frequency current is supplied as treatment energy to the blood vessel M to be grasped between the grasping pieces 13 and 14, through the first and second opposing surfaces 31 and 32, which are energy application sections. When a high-frequency current flow through the blood vessel M, heat is generated from the blood vessel M and the blood vessel M is coagulated by the generated heat. When the first grasping force is exerted on the blood vessel M as shown in FIG. 18, the blood vessel M is contracted to some extent in the open and close direction of the grasping pieces 13 and 14. When the blood vessel is contracted to some extent in the open and close direction of the grasping pieces 13 and 14, the first and second grasping pieces 13 and 14 close relative to each other, and the distance between the first and second opposing surfaces 31 and 32 (distance between the electrodes) is a first distance N1. On the other hand, when the second grasping force, which is larger than the first grasping force, is exerted on the blood vessel M as shown in FIG. 19, the blood vessel M is contracted further in the open and close direction of the grasping pieces 13 and 14. When the blood vessel M is contracted further in the open and close direction of the grasping pieces 13 and 14, the first and second grasping pieces 13 and 14 close further relative to each other, and the distance between the first and second opposing surfaces 31 and 32 (distance between the electrodes) is a second distance N2 that is smaller than the first distance N1. The current density of the high-frequency current flowing between the electrodes is in inverse proportion to the distance between the electrodes (distance between the first and second opposing surfaces 31 and 32). Thus, when the second grasping force is exerted on the blood vessel M, the distance between the electrodes becomes smaller than that in the case where the first grasping force is exerted on the blood vessel M and accordingly the current density of the high-frequency current flowing through the blood vessel M increases. When the current density of the high-frequency current flowing through the blood vessel M increases, the amount of heat generated from the blood vessel M increases. Since, therefore, even a blood vessel whose wall thickness T is small, such as a blood vessel of a pulmonary circulatory system, is grasped with a large grasping force (e.g. second grasping force) in the sealing treatment using high-frequency energy, the amount of heat generated from the blood vessel M increases. Thus, when high-frequency energy is applied to the blood vessel M, even though the wall thickness T of a blood vessel is small, sealing performance is improved further in sealing treatment, and treatment performance is improved further in treatment to cut a blood vessel open and simultaneously coagulate it. In the foregoing embodiment, the energy surgical instrument (1) includes a first grasping piece (13) and a second grasping piece (14) which can be opened and closed relative to each other, a blood vessel being grasped between the first grasping piece (13) and the second grasping piece (14) when the first grasping piece (13) and the second grasping piece are closed relative to each other. At least one of the first grasping piece (13) and the second grasping piece (14) is provided with an energy application section (31; 32; 31, 32) which applies treatment energy to the blood vessel grasped between the first grasping piece (13) and the second grasping piece (14) to treat the blood vessel. The energy surgical instrument (1) also includes a setting unit 51 that sets information regarding the wall thickness T of a blood vessel and a grasping force adjustment unit (41) which adjusts a grasping force to grasp the blood vessel between the first grasping piece (13) and the second grasping piece (14) to a first grasping force when the wall thickness T set by the setting unit 51 is larger than a predetermined thickness Tth and adjusts the grasping force to a second grasping piece, which is larger than the first grasping force, when the wall thickness T set by the setting unit 51 is equal to or smaller than the predetermined thickness Tth.

According to another aspect, the present disclosure relates to a treatment method using the energy surgical instrument. The treatment method includes:

closing a first grasping piece and a second grasping piece relative to each other to grasp a blood vessel between the first grasping piece and the second grasping piece;

setting information regarding a wall thickness of the grasped blood vessel;

adjusting a grasping force to grasp the blood vessel between the first grasping piece and the second grasping piece to a first grasping force when the set wall thickness is larger than a predetermined thickness and adjusting the grasping force to a second grasping force, which is larger than the first grasping force, when the set wall thickness is equal to or smaller than the predetermined thickness; and applying treatment energy to the treatment target to seal the treatment target.

Additional advantages and modifications will readily occur to those skilled in the art. Therefore, the broader aspects of the energy surgical instrument and related treatment method are not limited to the specific details and embodiments shown and described herein. Accordingly, various modifications may be made without departing from the spirit or scope of the general inventive concept as defined by the appended claims and their equivalents.

What is claimed is:

1. An energy surgical instrument comprising:
a first grasping piece;
a second grasping piece that is configured to open and close relative to the first grasping piece, the first grasping piece and the second grasping piece being configured to grasp a blood vessel therebetween, at least one of the first grasping piece and the second grasping piece being configured to apply treatment energy to the blood vessel grasped therebetween to treat the blood vessel;
a processor that is configured to set a wall thickness of the blood vessel and set whether the wall thickness of the blood vessel is greater than a predetermined thickness; and
a grasping force adjuster that is configured to adjust a grasping force applied by the first grasping piece and the second grasping piece to grasp the blood vessel therebetween,
wherein the instrument is configured to apply:
a first grasping force when the wall thickness set by the processor is larger than the predetermined thickness, and
a second grasping force, which is larger than the first grasping force, when the wall thickness set by the processor is equal to or smaller than the predetermined thickness.

2. The energy surgical instrument of claim 1, further comprising a detector that is configured to detect information regarding the blood vessel,
wherein the processor is configured to set the wall thickness based on the information detected by the detector.

3. The energy surgical instrument of claim 1, further comprising an operating panel,
wherein the processor is configured to set the wall thickness based on information regarding the blood vessel input through the operating panel.

4. The energy surgical instrument of claim 1, further comprising a controller that is configured to:
determine a magnitude of the grasping force to be applied by the first grasping piece and the second grasping piece based on the wall thickness set by the processor, and
control actuation of the grasping force adjuster in accordance with the determined magnitude.

5. The energy surgical instrument of claim 1, wherein:
the grasping force adjuster is configured to move between a first position and a second position; and
the instrument is configured to apply:
the first grasping force when the grasping force adjuster is in the first position, and
the second grasping force when the grasping force adjuster is in the second position.

6. The energy surgical instrument of claim 1, further comprising a handle configured to open and close relative to a grip to respectively open and close the second grasping piece relative to the first grasping piece,
wherein:
the grasping force adjuster is an abutment positioned on the grip such that when the handle closes relative to the grip, the handle abuts on the abutment; and
the abutment is configured to move in a longitudinal direction to adjust the grasping force.

7. The energy surgical instrument of claim 1, wherein:
the grasping force adjuster is a rod that abuts on a distal side of a ring member; and
the rod is configured to move in a radial direction of the ring member to control movement of the ring member in a distal direction and adjust the grasping force.

8. The energy surgical instrument of claim 1, wherein:
the first grasping piece is a distal portion of a rod;
the grasping force adjuster is a bar having a stopper positioned at a distal end thereof;
the stopper abuts on an outer surface of the rod to support the rod in an opening direction of the second grasping piece; and
the bar is configured to move relative to the rod to adjust the grasping force.

9. The energy surgical instrument of claim 1, wherein the first grasping piece is the grasping force adjuster and is configured to be rotated about a longitudinal axis of the instrument to adjust the grasping force.

10. The energy surgical instrument according to claim 2, wherein the detector comprises a pressure sensor provided on at least one of the first grasping piece and the second grasping piece.

11. The energy surgical instrument according to claim 10, wherein the processor is configured to determine that the wall thickness of the blood vessel is:
smaller than the predetermined thickness when a pressure detected by the pressure sensor is larger than or equal to a predetermined pressure, and
larger than the predetermined thickness when the pressure detected by the pressure sensor is smaller than the predetermined pressure.

12. The energy surgical instrument according to claim 11, wherein the pressure detected by the pressure sensor is larger than or equal to the predetermined pressure when the pressure sensor abuts an opposing surface of one of the first grasping piece and the second grasping piece.

13. The energy surgical instrument according to claim 2, wherein the detector comprises:
a first conductive member that is provided at a proximal portion of a first opposing surface of the first grasping piece; and
a second conductive member that is provided at a proximal portion of a second opposing surface of the second grasping piece, and is positioned to oppose the first conductive member.

14. The energy surgical instrument according to claim 13, wherein the processor is configured to determine that the wall thickness of the blood vessel is:
larger than the predetermined thickness when no current flows through the first conductive member and the second conductive member, and
equal to or smaller than the predetermined thickness when current flows through the first conductive member and the second conductive member.

15. The energy surgical instrument according to claim 2, wherein the detector comprises an angle sensor configured to detect an angle between the first grasping piece and the second grasping piece.

16. The energy surgical instrument according to claim 2, further comprising a light emitter provided on one of the first grasping piece and the second grasping piece, and configured to transmit light,
   wherein the detector comprises a light receiver that is provided on one of the first grasping piece and the second grasping piece, and is configured to detect an amount of light incident thereon.

17. A treatment method comprising:
closing the second grasping piece of the energy surgical instrument according to claim 1 relative to the first grasping piece to grasp the blood vessel therebetween; and
applying the treatment energy to the blood vessel grasped by the first grasping piece and the second grasping piece to seal the blood vessel,
wherein the grasping force applied by the first grasping piece and the second grasping piece to grasp the blood vessel therebetween is adjusted to:
   the first grasping force when the wall thickness set by the processor is larger than the predetermined thickness, and
   the second grasping force when the wall thickness set by the processor is smaller than or equal to the predetermined thickness.

18. The energy surgical instrument of claim 1, wherein the instrument is configured to apply:
   the first grasping force when the wall thickness set by the processor corresponds to a wall thickness of a blood vessel of a systemic circulatory system, which is larger than the predetermined thickness, and
   the second grasping force, which is larger than the first grasping force, when the wall thickness set by the processor corresponds to a wall thickness of a blood vessel of a pulmonary circulatory system, which is equal to or smaller than the predetermined thickness.

* * * * *